(12) United States Patent
Sherwood et al.

(10) Patent No.: US 10,770,182 B2
(45) Date of Patent: Sep. 8, 2020

(54) SYSTEMS AND METHODS FOR ASSESSING THE HEALTH STATUS OF A PATIENT

(71) Applicant: Cardiac Pacemakers, Inc., St. Paul, MN (US)

(72) Inventors: Gregory J. Sherwood, North Oaks, MN (US); Kyle Harish Srivastava, Saint Paul, MN (US); Bryan Allen Clark, Forest Lake, MN (US); Justin Theodore Nelson, St. Louis Park, MN (US); Carl Walter Bauer, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 77 days.

(21) Appl. No.: 15/982,506

(22) Filed: May 17, 2018

(65) Prior Publication Data

US 2018/0336970 A1    Nov. 22, 2018

Related U.S. Application Data

(60) Provisional application No. 62/508,442, filed on May 19, 2017.

(51) Int. Cl.
*G16H 50/30* (2018.01)
*G16H 10/65* (2018.01)
(Continued)

(52) U.S. Cl.
CPC .......... *G16H 50/30* (2018.01); *A61B 5/0022* (2013.01); *A61B 5/021* (2013.01); *A61B 5/0205* (2013.01);
(Continued)

(58) Field of Classification Search
CPC ........ G16H 10/65; G16H 50/20; G16H 50/30; A61B 5/0205; A61B 5/0022; A61B 5/082;
(Continued)

(56) References Cited

U.S. PATENT DOCUMENTS 3,661,528 A    5/1972  Falk
3,952,730 A    4/1976  Key
(Continued)

FOREIGN PATENT DOCUMENTS

CN    102941042    2/2013
CN    103332678    10/2013
(Continued)

OTHER PUBLICATIONS

International Preliminary Report on Patentability for PCT Application No. PCT/US2017/057318 dated May 2, 2019 (11 pages).
(Continued)

*Primary Examiner* — Carl H Layno
*Assistant Examiner* — Jane C Kalinock
(74) *Attorney, Agent, or Firm* — Pauly, DeVries Smith & Deffner LLC

(57) ABSTRACT

Embodiments herein include medical systems, devices, and methods for assessing the health status of a patient. In an embodiment, a method includes evaluating the presence of volatile organic compounds in a breath or gas sample of the patient with a plurality of graphene sensors to generate volatile organic compound data, wherein the plurality of graphene sensors include sensors that are specific for different volatile organic compounds. The method can further include collecting data regarding the patient's sympathetic nervous activity. The method can further include combining the volatile organic compound data with the collected data regarding the patient's sympathetic nervous activity to form
(Continued)

a combined data set. The method can further include matching the combined data set against one or more data patterns to find the best match, the best match indicating the health status of the patient. Other embodiments are also included herein.

19 Claims, 8 Drawing Sheets

(51) Int. Cl.
  *A61B 5/00*   (2006.01)
  *A61B 5/08*   (2006.01)
  *A61B 5/0205* (2006.01)
  *A61B 5/021*  (2006.01)
  *G16H 50/20*  (2018.01)
  *A61B 5/024*  (2006.01)

(52) U.S. Cl.
  CPC ............ *A61B 5/082* (2013.01); *A61B 5/681* (2013.01); *A61B 5/686* (2013.01); *G16H 10/65* (2018.01); *A61B 5/02405* (2013.01); *A61B 5/0816* (2013.01); *A61B 5/7264* (2013.01); *A61B 5/7275* (2013.01); *G16H 50/20* (2018.01)

(58) Field of Classification Search
  CPC ..... A61B 5/6861; A61B 5/7275; A61B 5/021; A61B 5/02405; A61B 5/0816; A61B 5/681; A61B 5/686; A61B 5/7264
  USPC ........................................................ 600/301
  See application file for complete search history.

(56) References Cited

U.S. PATENT DOCUMENTS

| | | |
|---|---|---|
| 3,981,297 A | 9/1976 | Dunn et al. |
| 4,901,727 A | 2/1990 | Goodwin |
| 5,174,290 A | 12/1992 | Fiddian-Green |
| 5,186,172 A | 2/1993 | Fiddian-Green |
| 5,357,971 A | 10/1994 | Sheehan et al. |
| 5,423,320 A | 6/1995 | Salzman et al. |
| 5,704,368 A | 1/1998 | Asano et al. |
| 5,834,626 A | 11/1998 | De Castro et al. |
| 5,928,155 A | 7/1999 | Eggers et al. |
| 6,006,121 A | 12/1999 | Vantrappen et al. |
| 6,029,076 A | 2/2000 | Fiddian-Greene et al. |
| 6,085,576 A | 7/2000 | Sunshine et al. |
| 6,149,624 A | 11/2000 | Mcshane |
| 6,192,168 B1 | 2/2001 | Feldstein et al. |
| 6,238,339 B1 | 5/2001 | Fiddian-Greene et al. |
| 6,248,078 B1 | 6/2001 | Risby et al. |
| 6,312,390 B1 | 11/2001 | Phillips |
| 6,480,734 B1 | 11/2002 | Zhang et al. |
| 6,599,253 B1 | 7/2003 | Baum et al. |
| 6,615,066 B2 | 9/2003 | Huyberechts et al. |
| 6,712,770 B2 | 3/2004 | Lin et al. |
| 6,726,637 B2 | 4/2004 | Phillips et al. |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B1 | 2/2007 | Turcott et al. |
| 7,426,848 B1 | 9/2008 | Li et al. |
| 7,459,312 B2 | 12/2008 | Chen et al. |
| 7,704,214 B2 | 4/2010 | Meixner et al. |
| 7,809,441 B2 | 10/2010 | Kane et al. |
| 7,871,572 B2 | 1/2011 | Yang et al. |
| 7,972,277 B2 | 7/2011 | Oki et al. |
| 7,992,422 B2 | 8/2011 | Leddy et al. |
| 8,043,860 B2 | 10/2011 | Leznoff et al. |
| 8,052,933 B2 | 11/2011 | Schirmer et al. |
| 8,080,206 B2 | 12/2011 | Leddy et al. |
| 8,124,419 B2 | 2/2012 | Grigorian et al. |
| 8,153,439 B2 | 4/2012 | Zamborini et al. |
| 8,154,093 B2 | 4/2012 | Passmore et al. |
| 8,157,730 B2 | 4/2012 | Tucker et al. |
| 8,222,041 B2 | 7/2012 | Pearton et al. |
| 8,244,355 B2 * | 8/2012 | Bennett ................ A61B 5/0205 600/301 |
| 8,366,630 B2 | 2/2013 | Haick et al. |
| 8,479,731 B2 | 7/2013 | Heinonen et al. |
| 8,481,324 B2 | 7/2013 | Nakhoul et al. |
| 8,494,606 B2 | 7/2013 | Debreczeny et al. |
| 8,529,459 B2 | 9/2013 | Stahl, Jr. et al. |
| 8,597,953 B2 | 12/2013 | Haick et al. |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Goldshtein et al. |
| 8,955,367 B2 | 2/2015 | Gouma et al. |
| 9,011,779 B1 | 4/2015 | Jensen et al. |
| 9,029,168 B2 | 5/2015 | Mannoor et al. |
| 9,103,775 B2 | 8/2015 | Bradley et al. |
| 9,147,851 B1 | 9/2015 | Bartsch et al. |
| 9,299,238 B1 | 3/2016 | Ahmad et al. |
| 9,315,848 B2 | 4/2016 | Haick et al. |
| 9,316,637 B2 | 4/2016 | Ren et al. |
| 9,324,825 B2 | 4/2016 | Ravesi et al. |
| 9,366,664 B2 | 6/2016 | Jensen et al. |
| 9,513,244 B2 | 12/2016 | Koester |
| 9,528,979 B2 | 12/2016 | Haick et al. |
| 9,618,476 B2 | 4/2017 | Goldsmith |
| 9,696,311 B2 | 7/2017 | Haick et al. |
| 9,765,395 B2 | 9/2017 | Goldsmith |
| 9,936,897 B2 | 4/2018 | Carlson et al. |
| 10,034,621 B2 | 7/2018 | Wondka et al. |
| 10,046,323 B2 | 8/2018 | Bos |
| 2002/0123749 A1 | 9/2002 | Jain et al. |
| 2002/0142477 A1 | 10/2002 | Lewis et al. |
| 2003/0051733 A1 | 3/2003 | Kotmel et al. |
| 2004/0039295 A1 | 2/2004 | Olbrich et al. |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2007/0265509 A1 | 11/2007 | Burch et al. |
| 2008/0021339 A1 | 1/2008 | Gabriel et al. |
| 2008/0038154 A1 | 2/2008 | Longbottom et al. |
| 2008/0146890 A1 | 6/2008 | Leboeuf et al. |
| 2008/0161709 A1 | 7/2008 | Bradley |
| 2008/0183910 A1 | 7/2008 | Natoli et al. |
| 2008/0228098 A1 | 9/2008 | Popov et al. |
| 2008/0317636 A1 | 12/2008 | Brahim et al. |
| 2009/0054799 A1 | 2/2009 | Vrtis et al. |
| 2009/0112115 A1 | 4/2009 | Huang et al. |
| 2010/0024533 A1 | 2/2010 | Kimura et al. |
| 2010/0056892 A1 | 3/2010 | Ben-Barak et al. |
| 2010/0085067 A1 | 4/2010 | Gabriel et al. |
| 2010/0137733 A1 | 6/2010 | Wang et al. |
| 2010/0147303 A1 | 6/2010 | Jafari et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0143962 A1 | 6/2011 | Chaubron et al. |
| 2011/0201956 A1 | 8/2011 | Alferness et al. |
| 2011/0269632 A1 | 11/2011 | Haick et al. |
| 2011/0283770 A1 | 11/2011 | Hok et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |

(56) References Cited

U.S. PATENT DOCUMENTS

| | | |
|---|---|---|
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0331723 A1 | 12/2013 | Hernandez-Silveira et al. |
| 2013/0334579 A1 | 12/2013 | Accardi et al. |
| 2014/0018691 A1 | 1/2014 | Mcneill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0145735 A1 | 5/2014 | Koester et al. |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0276168 A1 | 9/2014 | Satya et al. |
| 2014/0294675 A1 | 10/2014 | Melker et al. |
| 2014/0318535 A1 | 10/2014 | Bullock et al. |
| 2014/0378790 A1 | 12/2014 | Cohen |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0164373 A1 | 6/2015 | Davis et al. |
| 2015/0196251 A1 | 7/2015 | Outwater et al. |
| 2015/0257676 A1 | 9/2015 | Fries |
| 2015/0265184 A1 | 9/2015 | Wondka et al. |
| 2015/0295562 A1* | 10/2015 | Agarwal ............. H03K 3/011 73/23.3 |
| 2015/0301021 A1 | 10/2015 | Haick et al. |
| 2015/0307936 A1 | 10/2015 | Goldsmith |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1 | 11/2015 | Anglin et al. |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1* | 3/2016 | Kakkar ............. A61B 5/4842 600/484 |
| 2016/0109440 A1 | 4/2016 | Sherwood et al. |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0334381 A1 | 11/2016 | King-smith et al. |
| 2016/0370337 A1 | 12/2016 | Blackley |
| 2017/0014043 A1 | 1/2017 | Mcdonnell |
| 2017/0042435 A1 | 2/2017 | Vermeulen et al. |
| 2017/0053068 A1 | 2/2017 | Pillai et al. |
| 2017/0227491 A1* | 8/2017 | Johnson ............. G01N 33/5438 |
| 2017/0307562 A1 | 10/2017 | Goldsmith |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0110444 A1 | 4/2018 | Sherwood et al. |
| 2018/0328841 A1 | 11/2018 | Graham et al. |
| 2019/0025237 A1 | 1/2019 | Kelly et al. |
| 2019/0178837 A1 | 6/2019 | Xu et al. |
| 2019/0286866 A1 | 9/2019 | Gurt |

FOREIGN PATENT DOCUMENTS

| | | |
|---|---|---|
| EP | 1764153 | 3/2007 |
| EP | 1806414 | 7/2007 |
| EP | 3093653 | 11/2016 |
| EP | 3431977 | 1/2019 |
| JP | 2011102747 | 5/2011 |
| JP | 2016022415 | 2/2016 |
| JP | 2017123912 | 7/2017 |
| WO | 9947905 | 9/1999 |
| WO | 2001070114 | 9/2001 |
| WO | 2008088780 | 7/2008 |
| WO | 2009135070 | 11/2009 |
| WO | 2013095730 | 6/2013 |
| WO | 2013189502 | 12/2013 |
| WO | 2015191558 | 12/2015 |
| WO | 2016064740 | 4/2016 |
| WO | 2016105464 | 6/2016 |
| WO | 2017218464 | 12/2017 |
| WO | 2018075731 | 4/2018 |
| WO | 2018213564 | 11/2018 |

OTHER PUBLICATIONS

Response to Communication Pursuant to Article 94(3) EPC for European Patent Application No. 18180455.0 filed Jun. 6, 2019 (44 pages).

Response to Communication Pursuant to Rules 161(1) and 162 EPC for European Patent Application No. 17733246.7 filed May 29, 2019 (22 pages).

Response to Non-Final Rejection dated Feb. 15, 2019 for U.S. Appl. No. 14/883,895, submitted via EFS-Web on May 10, 2019, 10 pages.

Communication Pursuant to Article 94(3) EPC for European Patent Application No. 18180455.0 dated Feb. 11, 2019 (6 pages).

Deen, David A. et al., "Graphene-Based Quantum Capacitance Wireless Vapor Sensors," IEEE Sensors Journal, vol. 14, No. 5, May 2014 (8 pages).

Ebrish, M.A. et al., "Operation of multi-finger graphene quantum capacitance varactors using planarized local bottom gate electrodes," Applied Physics Letters, vol. 100, No. 14, Apr. 2012 (4 pages).

European Search Report for European Patent Application No. 18180455.0 dated Dec. 3, 2018 (5 pages).

First Office Action for Chinese Patent Application No. 201580056417.2 dated Feb. 11, 2019 (13 pages) with English summary.

International Preliminary Report on Patentability for PCT Application No. PCT/US2018/037144 dated Dec. 27, 2018 (7 pages).

Ma, Rui et al., "Acetone Sensing Using Graphene Quantum Capacitance Varactors," IEEE Sensors, Oct. 30, 2016 (3 pages).

Non-Final Office Action for U.S. Appl. No. 14/883,895 dated Feb. 15, 2019 (17 pages).

Opera, A. et al., "Integrated Temperature, Humidity and Gas Sensors on Flexible Substrates for Low-Power Applications," Sensors, Jan. 1, 2007 (4 pages).

Response to Advisory Action dated Dec. 3, 2018, for APPLICATION U.S. Appl. No. 14/883,895, submitted via EFS-Web on Dec. 14, 2018, 11 pages.

Response to Final Rejection dated Sep. 14, 2018, for U.S. Appl. No. 14/883,895, submitted via EFS-Web on Nov. 7, 2018, 11 pages.

Communication Pursuant to Article 94(3) EPC for European Patent Application No. 18180455.0 dated Jul. 15, 2019 (5 pages).

Final Office Action for U.S. Appl. No. 14/883,895 dated Jul. 18, 2019 (19 pages).

Response to Final Rejection dated Jul. 18, 2019 for U.S. Appl. No. 14/883,895, submitted via EFS-Web on Sep. 18, 2019, 10 pages.

Final Office Action for U.S. Appl. No. 14/883,895 dated Sep. 14, 2018 (16 pages).

(56) References Cited

OTHER PUBLICATIONS

International Search Report and Written Opinion for PCT Application No. PCT/US2018/033166 dated Oct. 2, 2018 (12 pages).
Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).
Arasaradnam, R. P. et al., "Review Article: Next Generation Diagnostic Modalities in Gastroenterology—Gas Phase Volatile compound biomarker detection," Alimentary Pharmacology and Therapeutics 2014; 39: 780-789 (10 pages).
Boots, Agnes W. et al., "The Versatile Use of Exhaled Volatile Organic Compounds in Human Health and Disease," J. Breath Res. 6 (2012) 027108 (21 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
Ebrish, M. A. et al., "Operation of Multi-Finger Graphene Quantum Capacitance Varactors using Planarized Local Bottom Gate Electrodes," Applied Physics Letters, A I P Publishing LLC, 2012 (5 pages).
"European Search Report," for Dutch Patent Application No. 2019492 dated Apr. 12, 2018 (10 pages).
"FDC1004 4-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments Aug. 2014—Revised Oct. 2016 (46 pages).
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews, 2012, 14:112(11), pp. 6156-6214.
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Report on Patentability," for PCT Application No. PCT/US2015/056243 dated May 4, 2017 (8 pages).
"International Search Report and Written Opinion," for PCT Application No. PCT/US2015/056243, dated Jan. 26, 2016 (12 pages).
"International Search Report and Written Opinion," for PCT Application No. PCT/US2017/037144 dated Oct. 6, 2017 (11 pages).
"International Search Report and Written Opinion," for PCT Application No. PCT/US2017/057318 dated Feb. 6, 2018 (14 pages).
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Li, Xiao et al., "Digital Health: Tracking Physiomes and Activity Using Wearable Biosensors Reveals Useful Health-Related Information," PLoS Biology 15.1 (2017): e2001402 (30 pages).
Ma, Rui et al., "Acetone Sensing Using Graphene Quantum Capacitance Varactors," 2016 IEEE Sensors, Orlando, FL, 2016 (3 pages).
"Mechanical Data," DGS (S-PDSO-G10) DSC0010B Package Outline, Example Board Layout, and Stencil Design. Texas Instruments 2016 (5 pages).
Nakhleh, Morad K. et al., "Diagnosis and Classification of 17 Diseases from 1404 Subjects via Pattern Analysis of Exhaled Molecules," ACS Nano 2017, 11, 112-125 (14 pages).
"Nano Mobile Healthcare Inc.," Company Profile on Reuters.com URL <http://www.reuters.com/finance/stocks/companyProfile?symbol=VNTH.PK> accessed Mar. 17, 2017 (2 pages).
"Non-Final Office Action," for U.S. Appl. No. 14/883,895 dated Apr. 30, 2018 (37 pages).
Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
"Response to Communication Pursuant to Rules 161(1) and 162 EPC," for European Patent Application No. 15790739.5 filed with the EPO dated Dec. 8, 2017 (14 pages).
"Response to Non-Final Office Action," for U.S. Appl. No. 14/883,895, dated Apr. 30, 2018 and filed with the USPTO Jul. 2, 2018 (18 pages).
"Standard Terms and Conditions for Evaluation Modules," Texas Instruments 2016 (5 pages).
Wang, David "FDC1004: Basics of Capacitive Sensing and Applications," Application Report SNOA927, Texas Instruments Dec. 2014 (12 pages).
Communication Pursuant to Article 94(3) EPC for European Patent Application No. 15790739.5 dated Dec. 17, 2019 (5 pages).
Communication Pursuant to Article 94(3) EPC for European Patent Application No. 18180455.0 dated Dec. 20, 2019 (3 pages).
Final Office Action for U.S. Appl. No. 15/787,985 dated Jan. 17, 2020 (16 pages).
Non-Final Office Action for U.S. Appl. No. 15/621,103 dated Feb. 21, 2020 (58 pages).
Office Action for Japanese Patent Application No. 2019-517196 dated Feb. 4, 2020 (5 pages) No English Translation.
Response to Communication Pursuant to Rules 161(1) and 162 EPC for European Patent Application No. 17794832.0 filed Dec. 6, 2019 (9 pages).
Response to Non-Final Rejection dated Nov. 27, 2019 for U.S. Appl. No. 14/883,895 submitted via EFS-Web on Feb. 5, 2020, 9 pages.
Response to Non-Final Rejection dated Oct. 10, 2019 for U.S. Appl. No. 15/787,985, submitted via EFS-Web on Jan. 7, 2020, 17 pages.
International Preliminary Report on Patentability for PCT Application No. PCT/US2018/033166 dated Nov. 28, 2019 (8 pages).
Non-Final Office Action for U.S. Appl. No. 14/883,895 dated Nov. 27, 2019 (16 pages).
Non-Final Office Action for U.S. Appl. No. 15/787,985 dated Oct. 10, 2019 (40 pages).
Response to Advisory Action dated Oct. 11, 2019 for U.S. Appl. No. 14/883,895, submitted via EFS-Web on Oct. 16, 2019, 10 pages.
Response to Communication Pursuant to Article 94(3) EPC for European Patent Application No. 18180455.0 filed Nov. 12, 2019 (9 pages).
Second Office Action for Chinese Patent Application No. 201580056417.2 dated Sep. 25, 2019 (6 pages) No English Translation.
Bhadra, Sharmista et al., "Non-destructive detection of fish spoilage using a wireless basic volatile sensor," Talanta, vol. 134, Dec. 25, 2014 pp. 718-723 (6 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
Final Office Action for U.S. Appl. No. 14/883,895 dated May 1, 2020 (19 pages).
International Search Report and Written Opinion for PCT Application No. PCT/US2019/063324 dated Mar. 27, 2020 (17 pages).
International Search Report and Written Opinion for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Navaneethan, Udayakumar et al., "Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).
Non-Final Office Action for U.S. Appl. No. 16/037,218 dated Apr. 29, 2020 (46 pages).

(56) References Cited

OTHER PUBLICATIONS

Olson, Eric J. et al., "Capacitive Sensing of Intercalated H2O Molecules Using Graphene," ACS Appl. Mater. Interfaces 2015, 7(46), 25804-25812 (29 pages).

Response to Communication Pursuant to Article 94(3) EPC for European Patent Application No. 15790739.5 filed Apr. 24, 2020 (16 pages).

Response to Communication Pursuant to Article 94(3) EPC for European Patent Application No. 18180455.0 filed Apr. 21, 2020 (24 pages).

Response to Final Rejection dated Jan. 17, 2020 for U.S. Appl. No. 15/787,985, submitted via EFS-Web on Apr. 9, 2020, 12 pages.

Third Office Action for Chinese Patent Application No. 201580056417.2 dated Feb. 18, 2020 (6 pages) No English Translation.

Zhang, Yao et al., "Capacitive Sensing of Glucose in Electrolytes using Graphene Quantum Capacitance Varactors," ACS Appl. Mater. Interfaces 2017, 9, 38863-38869 (7 pages).

Zhang, Yao et al., "Glucose Sensing with Graphene Varactors," IEEE Sensors, SENSORS 2016—Proceedings, Orlando, FL 2016 (3 pages).

Zhen, Xue et al., "Noncovalent Monolayer MOdification of Graphene Using Pyrene and Cyclodextrin Receptors for Chemical Sensing," ACS Applied Nano Materials 2018, vol. 1, No. 6 pp. 2718-2726 (9 pages).

\* cited by examiner

SYSTEMS AND METHODS FOR ASSESSING THE HEALTH STATUS OF A PATIENT

This application claims the benefit of U.S. Provisional Application No. 62/508,442, filed May 19, 2017, the content of which is herein incorporated by reference in its entirety.

FIELD

Embodiments herein relate to medical systems, devices and methods for assessing the health status of a patient.

BACKGROUND

In the process of providing health care, clinicians often make physical observations and run tests to gather data about a patient. After collecting data and analyzing other aspects, such as a given patient's health history, the clinician often forms a diagnosis and then selects a therapy to treat the diagnosed condition.

The ability of clinicians to gather data about a patient has increased rapidly over time as devices, assays, and associated procedures have advanced. Yet, clinicians are still a long distance away from having complete health information about each patient. As merely one issue, the ability to gather data from or about a patient declines significantly when the patent is not in a clinical environment. Further, for most patients, the amount of time they spend in a clinical environment is relatively small compared to the time spent away from clinics, thus greatly limiting opportunities to gather data. Another issue is that not all disease states are fully characterized in terms of what pieces of data, that could be gathered, will provide diagnostic insight regarding the disease state.

While clinicians may never have complete health information about each patient, it is possible to increase the accuracy of health assessments and/or diagnoses by improving the nature and quantity of data available to clinicians.

SUMMARY

Embodiments herein include medical systems, devices and methods for assessing the health status of a patient.

In a first aspect, a method of assessing the health status of a patient is included. The method can include evaluating the presence of volatile organic compounds in a breath or gas sample of the patient with a plurality of graphene sensors to generate volatile organic compound data. The plurality of graphene sensors can include sensors that are specific for different volatile organic compounds. The method can further include collecting data regarding the patient's sympathetic nervous activity. The method can further include combining the volatile organic compound data with the collected data regarding the patient's sympathetic nervous activity to form a combined data set. The method can further include matching the combined data set against one or more previously determined data patterns using a pattern matching algorithm to determine the data pattern that is the best match, wherein the specific previously determined data pattern that is the best match indicates the health status of the patient.

In a second aspect, in addition to or in place of other aspects herein, the one or more previously determined data patterns are created using a machine learning process.

In a third aspect, in addition to or in place of other aspects herein, the data regarding the patient's sympathetic nervous activity can be selected from the group consisting of heart rate variability (HRV), electrodermal activity (EDA), blood pressure, respiratory rate, respiratory sinus arrhythmia (RSA), and baroreceptor sensitivity (BRS).

In a fourth aspect, in addition to or in place of other aspects herein, a method can further include collecting data regarding the patient's functional status, the data selected from the group consisting of gait and accelerometry data, and adding data regarding the patient's functional status to the combined data set.

In a fifth aspect, in addition to or in place of other aspects herein, a method can further include collecting data regarding the patient's demographic features and adding data regarding the patient's demographic features to the combined data set.

In a sixth aspect, in addition to or in place of other aspects herein, collecting data regarding the patient's sympathetic nervous activity can be performed in a non-clinical setting and evaluating the presence of the volatile organic compounds can be performed in a clinical setting.

In a seventh aspect, in addition to or in place of other aspects herein, collecting data regarding the patient's sympathetic nervous activity can be performed with a wearable device.

In an eighth aspect, in addition to or in place of other aspects herein, collecting data regarding the patient's sympathetic nervous activity is performed over a time period of at least about 1 day.

In a ninth aspect, in addition to or in place of other aspects herein, collecting data regarding the patient's sympathetic nervous activity is performed with an implanted device.

In a tenth aspect, in addition to or in place of other aspects herein, the volatile organic compound data from the breath or gas sample of the patient is downloaded from an external breath sensing system onto at least one of a wearable device and an implantable device.

In an eleventh aspect, in addition to or in place of other aspects herein, the collected data regarding the patient's sympathetic nervous activity is uploaded from a wearable device to clinical diagnostic device.

In a twelve aspect, in addition to or in place of other aspects herein, one or more of the plurality of graphene sensors are chosen as controls on the collected data regarding the patient's sympathetic nervous activity.

In a thirteenth aspect, in addition to or in place of other aspects herein, the controls correlate with sympathetic nervous activity.

In a fourteenth aspect, in addition to or in place of other aspects herein, the method can include generating a notification if the measured values of the controls do not match the measured values of sympathetic nervous activity.

In a fifteenth aspect, in addition to or in place of other aspects herein, the collected data regarding the patient's sympathetic nervous activity reflects a baseline level of sympathetic nervous activity and changes over the baseline level of sympathetic nervous activity.

In a sixteenth aspect, in addition to or in place of other aspects herein, the plurality of graphene sensors can detect the presence of at least 10 different volatile organic compounds.

In a seventeenth aspect, a diagnostic health system is included herein. The diagnostic health system can include a communications circuit, a memory circuit, and a processor in electronic communication with the communication circuit and the memory circuit. The processor can be configured to combine volatile organic compound data with collected data regarding a patient's sympathetic nervous activity to form a combined data set. The processor can also be configured to match the combined data set against one or more previously determined data patterns using a pattern matching algorithm to determine a pattern that is the best match, wherein the specific previously determined pattern that is the best match indicates the health status of the patient. The processor can also be configured to report the health status of the patient based on the best pattern match.

In an eighteenth aspect, in addition to or in place of other aspects herein, the diagnostic health system is a wearable device and the volatile organic compound data is downloaded onto the wearable device from another device.

In a nineteenth aspect, in addition to or in place of other aspects herein, the diagnostic health system is disposed in a clinical environment and collected data regarding a patient's sympathetic nervous activity is uploaded to the diagnostic health system from a wearable device.

In a twentieth aspect, a diagnostic health system is included having a patient-specific device selected from the group consisting of a wearable device and an implanted device. The system can also include an external breath sensing system and a processor receiving data from the patient-specific device and the external breath sensing system. The patient-specific device can collect data regarding a patient's autonomic tone, or in some embodiments, more specifically, a patient's sympathetic nervous system activity. The external breath sensing system can collect data regarding the presence of volatile organic compounds in a breath or gas sample of the patient. The processor can be configured to combine the volatile organic compound data with the patient's sympathetic nervous activity data to form a combined data set. The processor can also be configured to match the combined data set against one or more previously determined data patterns using a pattern matching algorithm to determine a pattern that is the best match, wherein the specific previously determined pattern that is the best match indicates the health status of the patient. The processor can also be configured to report the health status of the patient based on the best pattern match.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
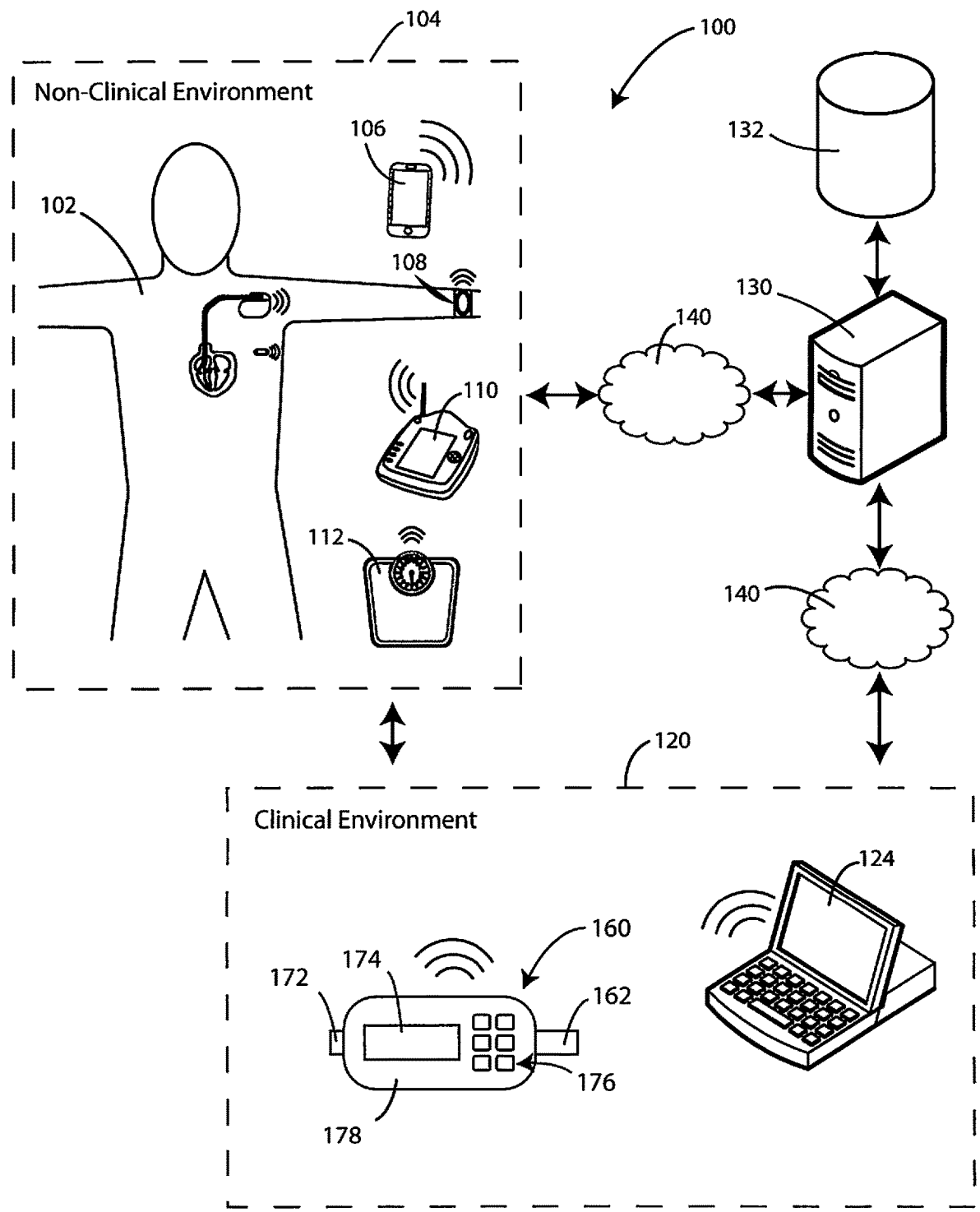
FIG. 1 is a schematic view of various components of a system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Volatile organic compounds, as sensed in breath samples or other gas samples, can provide valuable information about the health status of a patient. In particular, patterns of volatile organic compounds (including the presence, absence, and/or concentration of a plurality of different volatile organic compounds) in a breath or gas sample of a patient can be associated with various disease states and/or particular health statuses.

In some cases, though, the predictive power of a pattern of volatile organic compounds standing alone may have less than a desired level of accuracy. However, factors outside of the patient's breath or other gas sample can be leveraged to make the diagnostic more specific and sensitive.

Data regarding a patient's autonomic tone, or in some embodiments more specifically, a patient's sympathetic nervous system activity, can be used in combination with data regarding volatile organic compounds to enhance diagnostic specificity and/or sensitivity. For example, the onset of many illnesses are accompanied by increases in the body's sympathetic nerve activity. These changes can be detected directly or indirectly by using a number of physiological signals, including heart rate variability (HRV), electrodermal activity (EDA), factors related to the effect of sympathetic tone on vessel constriction (including, but not limited to, blood flow, perfusion, skin temperature, body temperature, blood pressure, and the like), respiratory rate, respiratory sinus arrhythmia (RSA), baroreceptor sensitivity (BRS), pupil diameter, and electrooculography. It will be appreciated that measurement of autonomic tone (e.g., parasympathetic/sympathetic balance) or measurement of parasympathetic tone can also be performed in addition to or instead of measurement of sympathetic nervous activity in some embodiments. Functional signals such as gait and accelerometry can also reveal small changes in health status. Many of these signals can be easily measured in an acute setting, such as when the patient is performing the breath sensor test in the clinic. However, in some cases these signals are recorded chronically, either before or after the breath or gas sensor test. In this way, the clinician is able to obtain a mean signal. Further details of data that can be gathered and/or used in accordance with embodiments herein are described below.

Data regarding the patient's sympathetic nervous activity can be collected over various time periods. In some embodiments, such data is collected over a time period of at least about 1 second, 5 seconds, 10 seconds, 30 seconds, 1 minute, 5 minutes, 15 minutes, 30 minutes, 45 minutes, 60 minutes, 2 hours, 4 hours, 8 hours, 12 hours, 24 hours, 3 days, 5 days, 7 days, 9 days, 11 days, 13 days, 15 days, 30 days, 45 days, 60 days, 90 days, or 120 days. In some embodiments, the patient's sympathetic nervous activity can be collected over a time period in a range wherein any of the foregoing amounts of time can serve as the upper or lower bound of the range, provided that the upper bound is greater than the lower bound.

Thus, in accordance with various embodiments herein, other types of data can combined with data regarding volatile organic compounds in order to improve the overall accuracy of assessments of the patient's health status. In particular, data regarding the sympathetic nervous state of a patient can be combined with volatile organic compound data in order to improve the accuracy of assessments of the patient's health status and/or disease state. For example, such combined data can be used to detect the signature of a medical condition. The medical condition can be any disease state including, but not limited to, lung cancer, colon cancer, pulmonary disease (e.g. asthma, COPD), cardiovascular disease (e.g. heart failure), digestive and inflammatory diseases (e.g. inflammatory bowel diseases such as Crohn's, colitis, or the like) or diabetes.

Volatile organic data can be gathered in various settings including non-clinical settings and clinical settings. Similarly, data regarding the sympathetic nervous state of a patient can be gathered in various settings including non-clinical settings and clinical settings.

In some cases, data gathered in a non-clinical setting can be combined with data gathered in a clinical setting. For example, data gathered in a clinical setting (such as breath or gas analysis data) can be downloaded to a wearable or implantable device where further operations relying upon the downloaded data can be executed by the wearable or implantable device. However, in other examples, data gathered in a non-clinical setting (such as data regarding the sympathetic nervous state of a patient) can be uploaded to a device (testing device, system or computer) in a clinical setting and then further operations relying upon the uploaded data can be executed by the device in the clinical setting.

Referring now to FIG. 1, a schematic view is shown of possible components of a system 100 in accordance with various embodiments herein. The system 100 can include external patient specific devices within a non-clinical environment 104 (or ambulatory setting) including, but not limited to, a smart phone 106, a wearable device 108, and a patient-specific data gathering device 112, such as a weight scale. The non-clinical environment 104 can also include devices implanted within the patient 102 (discussed in greater detail with respect to FIGS. 2-3 below).

The non-clinical environment 104 can also include a patient communicator 110 (or patient management device). An exemplary patient management system is the LATITUDE® patient management system, commercially available from Boston Scientific Corporation, Natick, Mass. Aspects of an exemplary patient management system are described in U.S. Pat. No. 6,978,182, the content of which is herein incorporated by reference.

The system 100 can also include devices within a clinical environment 120 (or non-ambulatory setting) including, but not limited to, a programmer device 124 that can be used to send data to and/or receive data from implanted devices as well as from other devices across a network.

The clinical environment 120 can also include a breath sensing system 160 for sensing gaseous analytes (or volatile organic compounds) in accordance with various embodiments herein. In this embodiment, the system is in a handheld format. It will be appreciated, however, that many other formats for the system are contemplated herein.

The breath sensing system 160 can include a housing 178. The system 160 can include a mouthpiece 162 into which a subject to be evaluated can blow a breath sample. The system 160 can also include a display screen 174 and a user input device 176, such as a keyboard. The system can also include a gas outflow port 172. Aspects of breath sensing systems are described in U.S. Publ. Appl. No. 2016/0109440, the content of which is herein incorporated by reference. While FIG. 1 shows a breath sensing system, it will be appreciated that other types of gas sampling systems can also be used herein. For example, gas sampling devices for use with catheters and endoscopy systems can also be used. An exemplary gas sampling system in the context of a catheter or endoscopy device is described in U.S. Appl. No. 62/350,345, the content of which is herein incorporated by reference.

Devices and systems in the clinical environment 120 can communicate with devices and systems in the non-clinical environment 104 for the exchange of data. Devices and systems in both the clinical environment 120 and the non-clinical environment 104 can also communicate with computing devices in remote locations through a data network 140, such as the Internet or another network for the exchange of data as packets, frames, or otherwise.

In some embodiments, the system 100 can also include a computing device such as a server 130 (real or virtual). In some embodiments, the server 130 can be located remotely from the non-clinical environment 104 and/or the clinical environment 120. The server 130 can be in data communication with a database 132.

The database 132 can be used to store various patient information, such as that described herein. In some embodiments, the database can specifically include an electronic medical database containing data regarding the health status of a patient, patterns of data associated with various conditions (such as that generated from machine learning analysis of large sets of patient data), demographic data and the like.

The server 130 can be in data communication with the non-clinical environment 104 and/or the clinical environment 120 through a network such as the Internet or another public or private data network including packet switched data networks or non-packet switched data networks. In some embodiments, the server 130 can be located in proximity to non-clinical environment 104 and/or the clinical environment 120.

As described above, FIG. 1 shows devices in a non-clinical environment 104 as well as a clinical environment 120. However, it will be appreciated that some devices shown in the non-clinical environment can also be present in and used in a clinical environment. Similarly, some devices shown in the clinical environment can be present in and used in a non-clinical environment. In addition, some systems herein do not include all of the various elements shown in FIG. 1. Also, in some cases, systems herein can include additional components not shown in FIG. 1.

Figure 2:
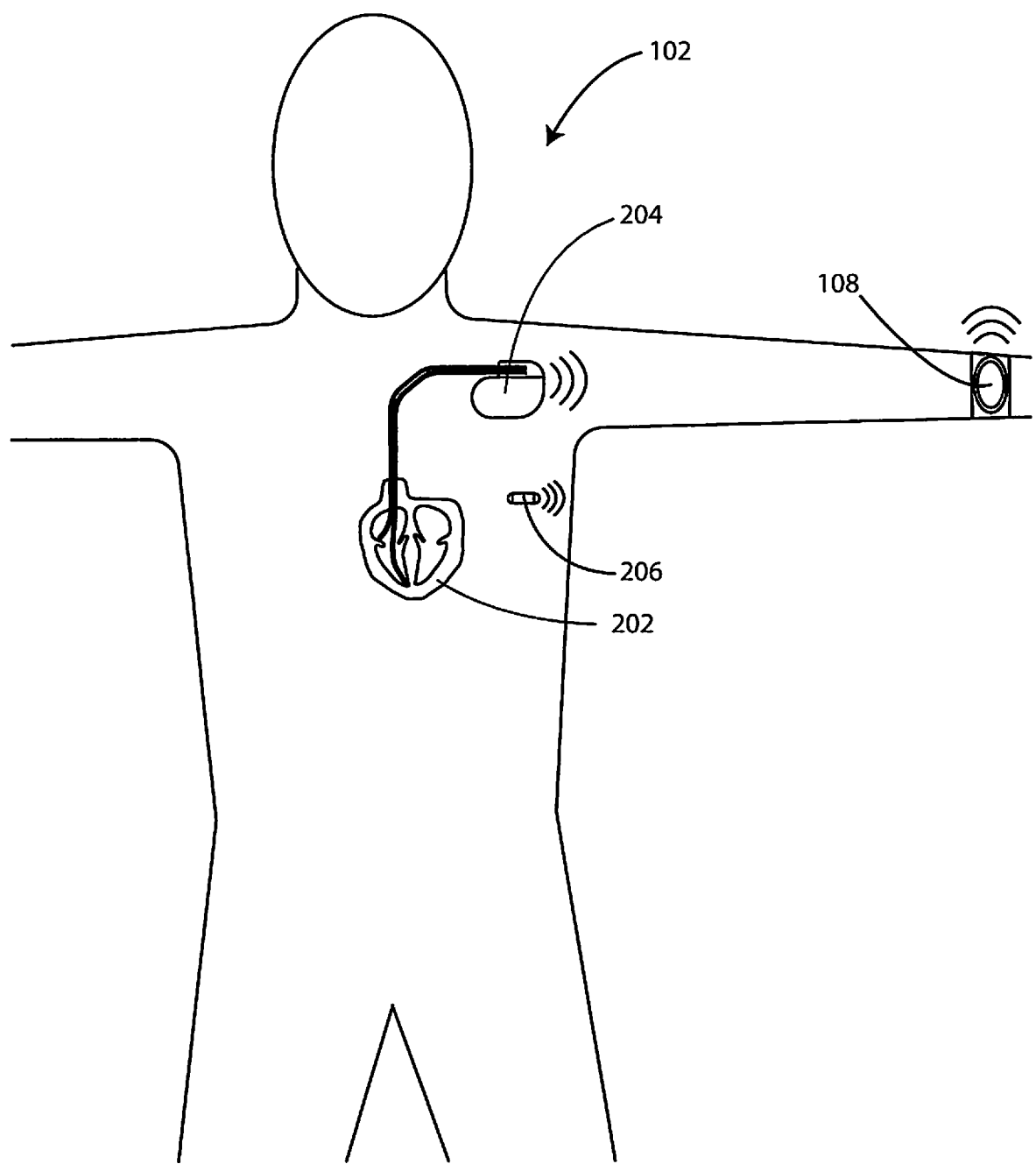
FIG. 2 is a schematic view of a patient and various devices associated with the patient.

Referring now to FIG. 2, a schematic view is shown of patient 102 and various devices that can be associated with a patient 102. The patient 102 can have various implanted devices and/or various external devices. In specific, the patient 102 can utilize a wearable device 108. While the wearable device 108 in FIG. 2 is on the patient's 102 wrist, it will be appreciated that this is merely one example and the device can also be worn on other parts of the patient 102. The wearable or other external devices can provide various functionality. In some embodiments, the wearable device(s) can include sensors, such as any of the types of sensors described herein. The wearable device(s) can specifically be used to gather data regarding the sympathetic nervous state of a patient (of subject).

In some embodiments, the wearable or other external device can be used to provide alerts to the patient and/or to care providers located in the same place as the patient or remotely. Alerts can take various forms. In some embodiments, the alert can be an audio and/or visual alert. In some embodiments, the wearable or other external device can be used to display information to the patient and/or to care providers. In some embodiments, the wearable or other external devices can be used to provide a prompt to the patient in order to get them to take some action in order to gather data.

Beyond external devices, there may also be implanted devices associated with the patient to gather data. For example, in some embodiments the patient 102 can have an implanted cardiac device 204. In some embodiments, the implanted cardiac device 204 can be connected to leads for sensing and/or electrical stimulation that can be disposed in or near the patient's heart 202. The implanted cardiac device 204 can include various sensors and/or can be connected to various sensors.

In some embodiments, an implanted monitoring/sensing device 206 can be implanted within the patient 102. Further details of an exemplary implanted monitoring/sensing device 206 are provided below with respect to FIG. 3 and the accompanying description. However, it will be appreciated that there are many different types of implanted devices that can be used with systems herein.

Figure 3:
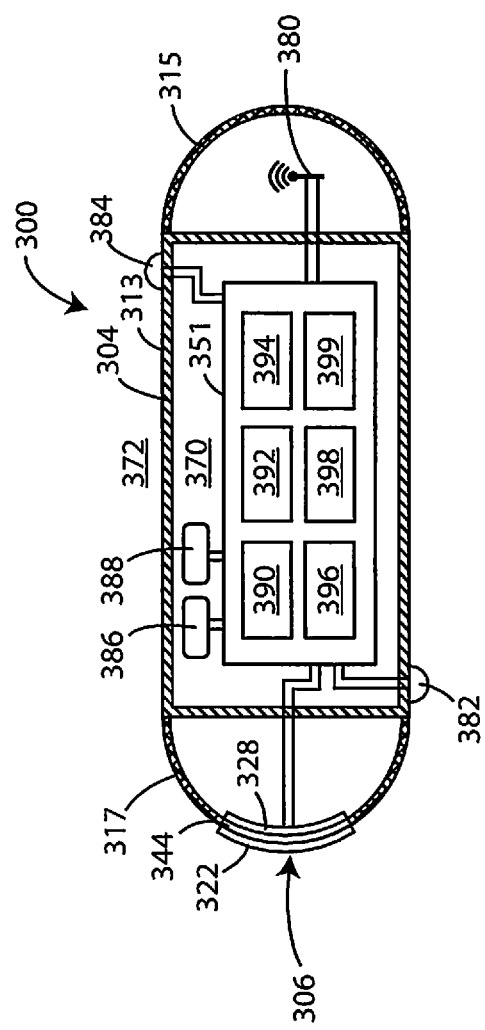
FIG. 3 is a schematic cross-sectional view of an exemplary sensor/monitor device.

Embodiments of systems herein can include sensor/monitor devices. Referring now to FIG. 3, a schematic cross-sectional view of an exemplary sensor/monitor device 300 is shown in accordance with various embodiments herein. The sensor/monitor device 300 includes a housing 304. The housing 304 of the sensor/monitor device 300 can include various materials such as metals, polymers, ceramics, and the like. In some embodiments, the housing 304 can be a single integrated unit. In other embodiments, the housing 304 can include a main segment 313 along with appendage segments 315 and 317. In one embodiment, the housing 304, or one or more portions thereof, is formed of titanium. In some embodiments, one or more segments of the housing 304 can be hermetically sealed. In some embodiments, the main segment 313 is formed of a metal and the appendage segments 315 and 317 are formed from a polymeric material.

The housing 304 defines an interior volume 370 that in some embodiments is hermetically sealed off from the area 372 outside of the sensor/monitor device 300. The sensor/monitor device 300 can include circuitry 351. The circuitry 351 can include various components, such as components 390, 392, 394, 396, 398, and 399. In some embodiments, these components can be integrated, and in other embodiments, these components can be separate. In some embodiments, the components can include one or more of a microprocessor, memory circuitry (such as random access memory (RAM) and/or read only memory (ROM)), recorder circuitry, telemetry circuitry, sensor and/or sensor interface circuitry, power supply circuitry (which can include one or more batteries), normalization circuitry, control circuitry, evaluation circuitry, and the like. In some embodiments, recorder circuitry can record the data produced by the various sensors and record time stamps regarding the same. In some embodiments, the circuitry can be hardwired to execute various functions while in other embodiments, the circuitry can be implemented as instructions executing on a microprocessor or other computation device.

The sensor/monitor device 300 can include, for example, an electrical field sensor that is configured to generate a signal corresponding to cardiac electric fields. The electrical field sensor can include a first electrode 382 and a second electrode 384. In some embodiments, the housing 304 itself can serve as an electrode. The electrodes can be in communication with the electrical field sensor. The electrical field sensor can include a circuit in order to measure the electrical potential difference (voltage) between the first electrode 382 and the second electrode 384. The electrical field sensor can include a circuit in order to measure the impedance between the first electrode 382 and the second electrode 384. The sensor/monitor device 300 can also include an antenna 380, to allow for unidirectional or bidirectional wireless data communication.

In some embodiments, the sensor/monitor device 300 can also include a chemical sensor 306. In the embodiment shown in FIG. 3, the chemical sensor can be an optical chemical sensor. However, in other embodiments, the chemical sensor can be a potentiometric chemical sensor. The chemical sensor 306 can specifically include a chemical sensing element 322, an optical window 344, and an electro-optical module 328. The electro-optical module 328 can be in electrical communication with the circuitry 351 within the interior volume 370, and in some embodiments, the circuitry 351 is configured to selectively activate the chemical sensor 306. The chemical sensor 306 can be configured to be chronically implanted.

The chemical sensor 306 can include an electro-optical module 328 coupled to the optical window 344. The electro-optical module 328 can specifically include one or more optical excitation assemblies. Each optical excitation assembly can include various light sources such as light-emitting diodes (LEDs), vertical-cavity surface-emitting lasers (VC-SELs), electroluminescent (EL) devices, or the like. The electro-optical module 328 can also include one or more optical detection assemblies. Each optical detection assembly can include one or more photodiodes, avalanche photodiodes, a photodiode array, a photo transistor, a multi-element photo sensor, a complementary metal oxide semiconductor (CMOS) photo sensor, or the like.

The chemical sensing element 322 can be disposed on or over the optical window 344. The chemical sensing element 322 can be configured to detect a physiological analyte by exhibiting an optically detectable response to the physiological analyte. Specific examples of physiological analytes are discussed in greater detail below. In operation, analytes of interest from the in vivo environment can diffuse into the chemical sensing element 322 causing a detectable change in the optical properties of the chemical sensing element 322. Light can be generated by the electro-optical module 328 and can pass through the optical window 344 and into the chemical sensing element 322. Light can then either be preferentially reflected from or re-emitted by the chemical sensing element 322 proportional to the sensed analyte and pass back through the optical window 344 before being received by the electro-optical module 328. Various aspects of exemplary chemical sensors are described in greater detail in U.S. Pat. No. 7,809,441, the content of which is herein incorporated by reference in its entirety.

In some embodiments the chemical sensing element 322 is located in a fluid such as blood, interstitial fluid, urine, lymph or chyle and senses analytes in the fluid. In other embodiments, the chemical sensing element 322 is located in a solid tissue such as muscle, fat, bone, bone marrow, organ tissues (e.g. kidney, liver, brain, lung, etc.) and senses analytes in the solid tissue.

Figure 4:
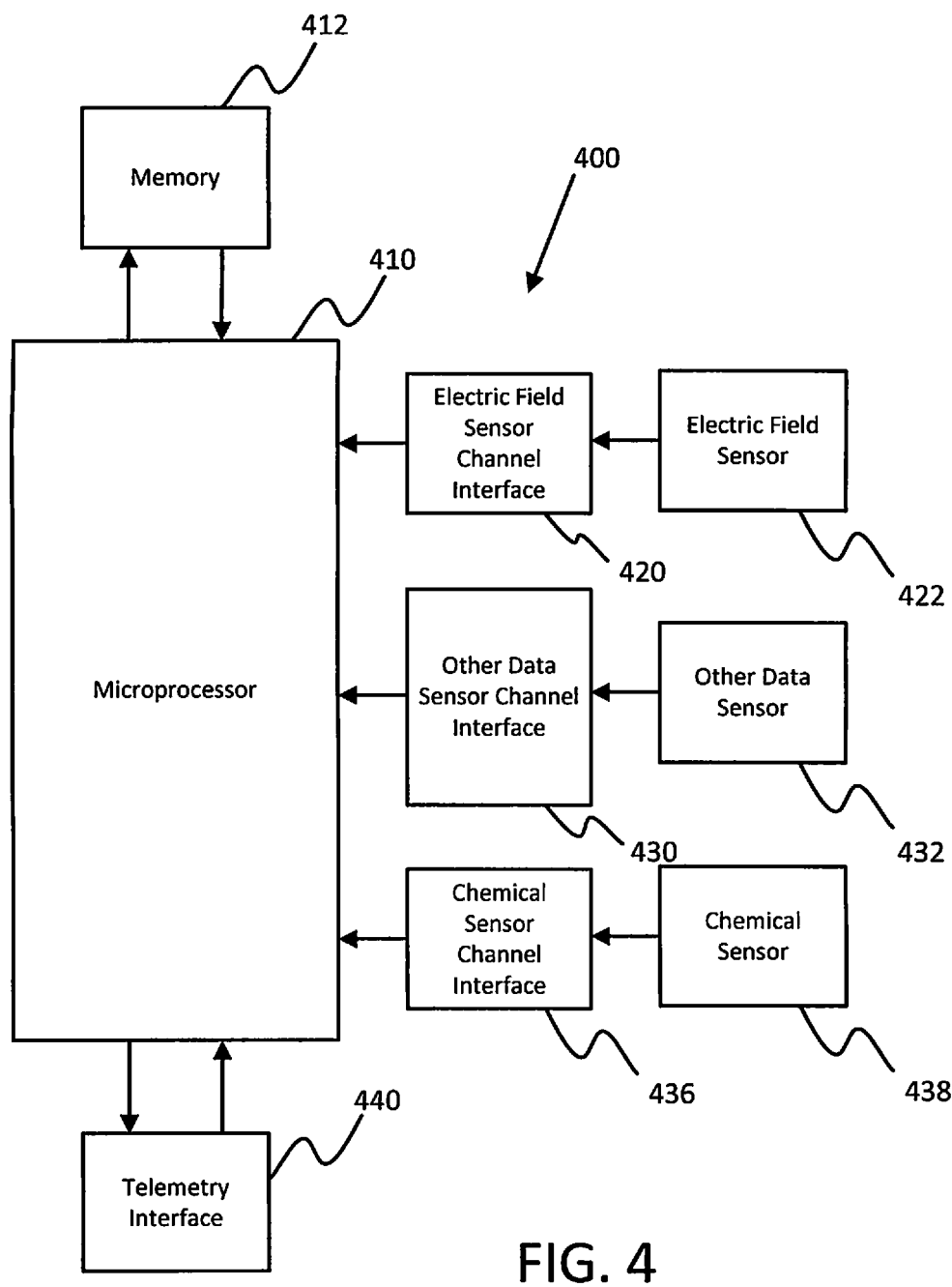
FIG. 4 is a schematic view of elements of a sensor/monitor device in accordance with various embodiments herein.

Elements of various devices (such as external wearable devices and/or implanted devices) that can be used as part of systems herein are shown in FIG. 4. However, it will be appreciated that some embodiments devices used herein with systems can include additional elements beyond those shown in FIG. 4. In addition, some embodiments of devices used with systems herein may lack some elements shown in FIG. 4. The device 400 (which can be implanted or external) can gather information through one or more sensing channels. A microprocessor 410 can communicate with a memory 412 via a bidirectional data bus. The memory 412 can include read only memory (ROM) or random access memory (RAM) for program storage and RAM for data storage.

The device 400 can include one or more electric field sensors 422 (in some cases, electrodes) and an electric field sensor channel interface 420 (for measuring impedance, electrical potential, or other electrical properties) which can communicate with a port of microprocessor 410. The device 400 can also include one or more other sensor(s) 432 and other sensor channel interface 430 which can communicate with a port of microprocessor 410.

The other sensors (implantable, wearable, or non-wearable external) can include, but are not limited to, one or more of a motion sensor, a posture sensor, an activity sensor, a respiration sensor, a pressure sensor (including blood pressure and/or urine pressure), flow sensor, impedance sensor, and any of the other types of sensors discussed herein.

The device 400 can also include a chemical sensor 438 and a chemical sensor channel interface 436 which can communicate with a port of microprocessor 410. The sensor channel interfaces 420, 430 and 436 can include various components such as analog-to-digital converters for digitizing signal inputs, sensing amplifiers, registers which can be written to by the control circuitry in order to adjust the gain and threshold values for the sensing amplifiers, and the like. A telemetry interface (or telemetry circuit) 440 is also provided for communicating with other devices of a system such as a programmer, a home-based unit and/or a mobile unit (e.g., a cellular phone).

Figure 5:
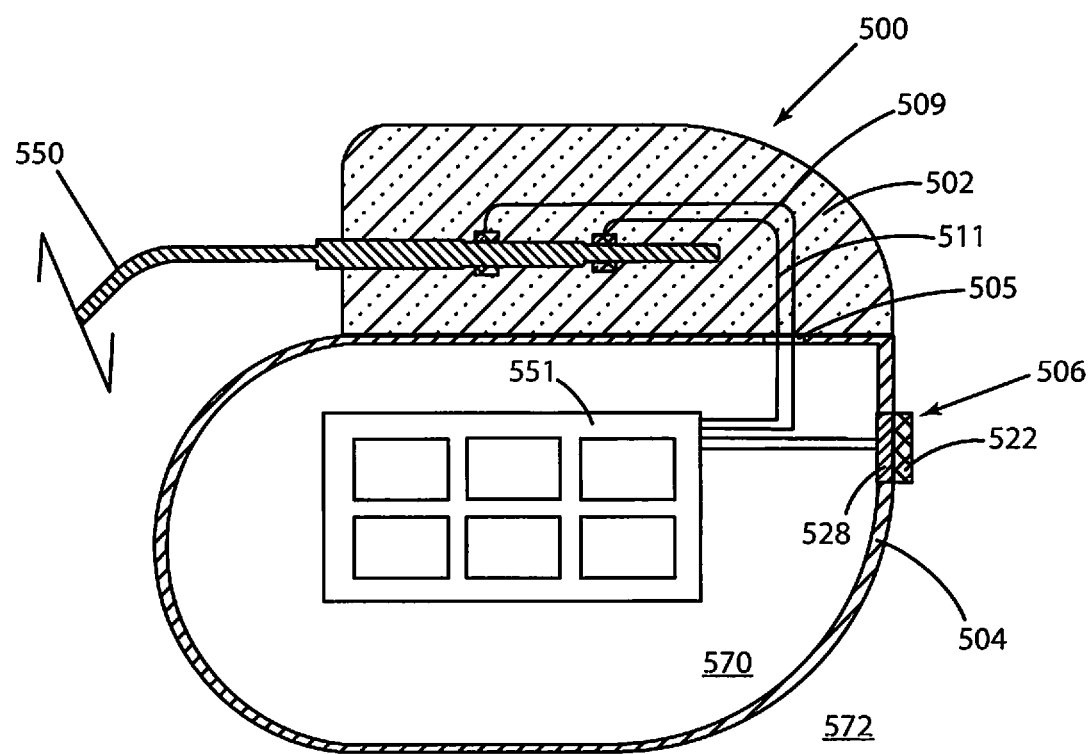
FIG. 5 is a schematic cross-sectional view of an implantable medical device in accordance with various embodiments herein.

Data herein can also be gathered by various other types of implantable medical devices, including but not limited to implantable cardiac devices. Referring now to FIG. 5, a schematic cross-sectional view of an implantable medical device 500 is shown in accordance with various embodiments herein. The implantable medical device 500 includes a header assembly 502 and a housing 504. The housing 504 of the implantable medical device 500 can include various materials such as metals, polymers, ceramics, and the like. In one embodiment, the housing 504 is formed of titanium. The header assembly 502 can be coupled to one or more electrical stimulation leads 550. The header assembly 502 serves to provide fixation of the proximal end of one or more leads and electrically couples the leads to components within the housing 504. The header assembly 502 can be formed of various materials including metals, polymers, ceramics, and the like.

The housing 504 defines an interior volume 570 that is hermetically sealed off from the volume 572 outside of the device 500. Various electrical conductors 509, 511 can pass from the header 502 through a feed-through structure 505, and into the interior volume 570. As such, the conductors 509, 511 can serve to provide electrical communication between the electrical stimulation lead 550 and control circuitry 551 disposed within the interior volume 570 of the housing 504. The control circuitry 551 can include various components such as a microprocessor, memory (or memory circuit) (such as random access memory (RAM) and/or read only memory (ROM)), a telemetry module, electrical field sensor and stimulation circuitry, a power supply (such as a battery), and an optical sensor interface channel, amongst others. The control circuitry 551 can include the evaluation circuitry in various embodiments herein.

The implantable medical device 500 can incorporate, for example, an electrical field sensor that is configured to generate a signal corresponding to cardiac electric fields. The electrical field sensor (for measuring impedance, electrical potential, or other electrical properties) can include a first electrode and a second electrode. The electrodes of the electrical field sensor can be the same electrodes used to provide electrical stimulation or can be different electrodes. In some embodiments, one or more electrodes can be mounted on one or more electrical stimulation leads 550. In some embodiments, the housing 504 can serve as an electrode. The electrodes can be in communication with the electrical field sensor and stimulation circuitry. The electrical field sensor can include a circuit (such as within control circuitry 551) in order to measure the electrical potential difference (voltage) between the first electrode and the second electrode. In some embodiments, the data from the electrical field sensor can be used to generate an electrocardiogram.

The implantable medical device 500 can also include a chemical sensor 506. In the embodiment shown in FIG. 5, the chemical sensor 506 is a potentiometric chemical sensor. The chemical sensor 506 can specifically include a receptor module 522, and a transducer module 528. The transducer module 528 can be in electrical communication with the circuitry 551 within the interior volume 570, and in some embodiments, the control circuitry 551 is configured to selectively activate the chemical sensor 506. The chemical sensor 506 can be configured to be chronically implanted.

The chemical sensor 506 can be configured to detect a physiological analyte by exhibiting an electrical signal response to the physiological analyte. In operation, analytes of interest from the in vivo environment can contact the receptor module 522 causing a detectable change in the electrical properties of the same. The transducer module 528 can then be used to process and/or propagate the signal created by the receptor module 522. While medical device 500 is described as being implantable, it will be appreciated that some or all of the same components and functionality can be included in an external and/or wearable medical device.

Figure 6:
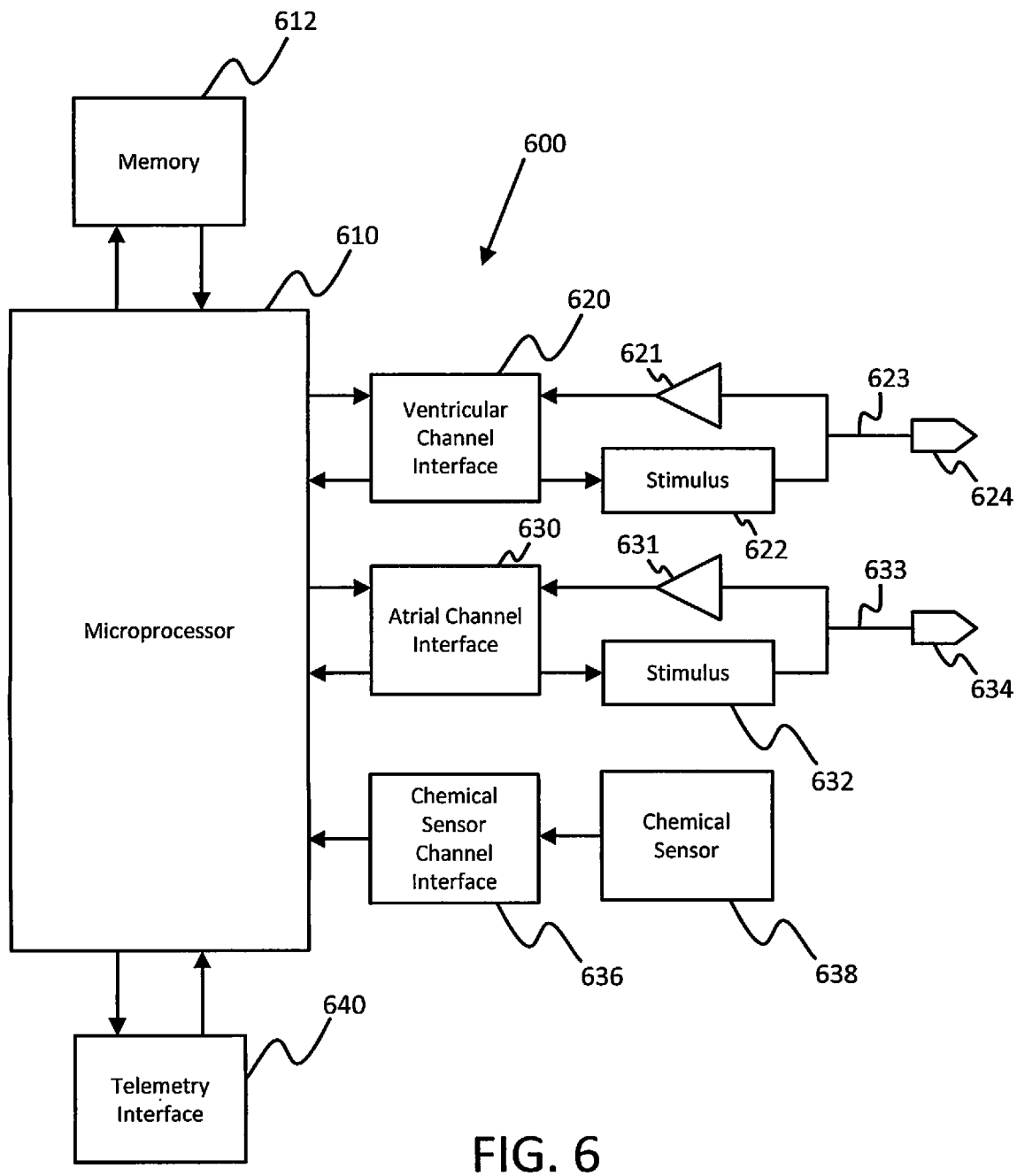
FIG. 6 is a schematic view of elements of an implantable medical device in accordance with some embodiments herein.

Elements of some embodiments of an implantable medical device that can be part of systems herein are shown in FIG. 6. However, it will be appreciated that some embodiments can include additional elements beyond those shown in FIG. 6. In addition, some embodiments may lack some elements shown in FIG. 6. The medical device 600 can sense cardiac events through one or more sensing channels and can output pacing pulses to the heart via one or more pacing channels in accordance with a programmed pacing mode. A microprocessor 610 communicates with a memory 612 via a bidirectional data bus. The memory 612 typically comprises read only memory (ROM) or random access memory (RAM) for program storage and RAM for data storage.

The implantable medical device can include atrial sensing and pacing channels comprising at least a first electrode 634, a lead 633, a sensing amplifier 631, an output circuit to provide a stimulus 632, and an atrial channel interface 630 which can communicate bidirectionally with a port of microprocessor 610. In this embodiment, the device 600 also has ventricular sensing and pacing channels comprising at least a second electrode 624, a lead 623, a sensing amplifier 621, an output circuit to provide a stimulus 622, and ventricular channel interface 620. For each channel, the same lead and electrode are used for both sensing and pacing. The channel interfaces 620 and 630 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device 600 can also include a chemical sensor 638 and a chemical sensor channel interface 636. A telemetry interface 640 is also provided for communicating with an external programmer or another implanted medical device.

Figure 7:
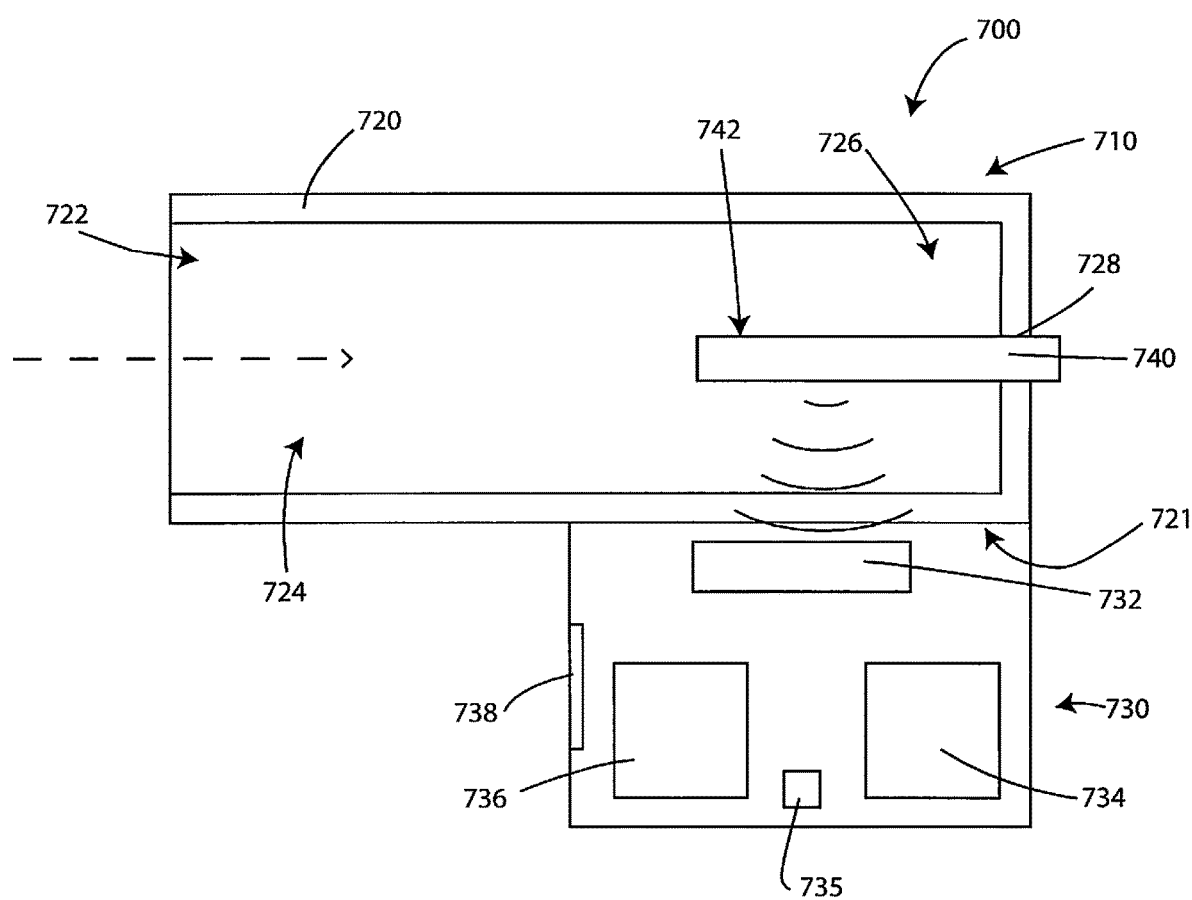
FIG. 7 is a schematic cross-sectional view of elements of a gas sensing device consistent with the technology disclosed herein.

Systems herein can also include a breath and/or gas sensing device or system. In particular, systems herein can gather data on the presence, absence, and/or amount of various gaseous analytes including, but not limited to, volatile organic compounds. FIG. 7 is a schematic cross-sectional view of an example system 700 consistent with the technology disclosed herein. It will be appreciated that this schematic view has been simplified for ease of illustration and that embodiments of systems and devices herein can include various features not shown in FIG. 7. In addition, some embodiments of systems and devices herein may lack various features shown in FIG. 7. The system 700 is generally configured for collecting a gas sample and communicating data associated with the gas sample. The system 700 has a gas sampling device 710 and a docking station 730.

The gas sampling device 710 can be configured to collect a gas sample and facilitate testing of the gas sample to generate data. In some embodiments, the gas sampling device 710 can be configured as a handheld device. In such cases, the gas sampling device can be configured to be held in the hand of a care provider, a patient, or both, during certain steps of its use, while also being configured to be held or otherwise positioned in association with the docking station 730 during certain steps of its use.

In some embodiments, the gas sampling device 710 is configured to receive a gas sample, such as exhaled breath, from a patient and direct the gas sample to a testing location. The gas sampling device 710 generally has a housing 720 defining an airflow aperture 722, a gas testing chamber 726, a sensor receptacle 728, an airflow pathway 724, and a docking structure 721.

When receiving a gas sample, the gas (such as breath from a patient), can pass into the gas sampling device 710 through the airflow aperture 722, through the airflow pathway 724, into the gas testing chamber 726 and into contact with one or more measurement zones 742 of a disposable sensor test strip 740, and then out the end of the gas testing chamber 726 through the sensor receptacle 728, or through a separate exhaust port (not shown in this view). While this view depicts contact between the sensor receptacle 728 and the disposable sensor test strip 740, it will appreciated that there can be segments or areas where the sensor receptacle 728 and the disposable sensor test strip 740 do not contact or do not create sealing contact, thus allowing for a path for the gas to flow out through the sensor receptacle 728.

While FIG. 7 shows the airflow pathway 724 to be approximately the same size as the interior space of the housing 720, it will be appreciated that this is simply for ease of illustration and that the size of the airflow pathway 724 can be, in many cases, much smaller than the entire interior size of the housing 720, allowing for room for other components within the interior of the housing 720, such as other components described herein including, but not limited to, sensors, a power source, processing devices, communication hardware, conditioning elements, and the like.

The housing 720 can be constructed of a variety of materials and combinations of materials. The housing 720 can be a single cohesive structure or can be constructed of multiple components that are coupled to form the housing 720. As an illustrative example, a portion of the housing 720 that defines the airflow pathway 724 can be coupled to the portion of the housing 720 that defines the airflow aperture 722. The portion of the housing 720 that defines the airflow pathway 724 can include a conduit or tube with various different cross-sectional sizes and shapes. The conduit or tube can be formed from various materials including, but not limited to, polymers, metals, ceramics, glass, composites or the like. In some embodiments, surfaces lining the airflow pathway 724 can be coated with materials to provide various desirable functional properties.

The airflow aperture 722 is generally configured to provide an input for the gas sample at the housing 720. In some embodiments the airflow aperture 722 is configured to be in fluid communication with a patient's mouth, although in some other embodiments a protective liner can be used to provide a barrier between the patient's mouth and the housing, which will be described in more detail, below.

The airflow pathway 724 generally is configured to direct the gas input at the airflow aperture 722 to the gas testing chamber 726. As such, the airflow pathway 724 generally extends from the airflow aperture 722 to the gas testing chamber 726. The airflow pathway 724 can have a cross-sectional area that is substantially the same along the length of the airflow pathway or it can vary. In some embodiments, the gas testing chamber 726 can have different interior dimensions (e.g., height, width, etc.) than the airflow pathway leading to it.

The gas testing chamber 726 defines a testing location for the gas sample. In various embodiments, the gas testing chamber 726 is configured to receive a measurement zone 742 of a disposable sensor test strip 740. Accordingly, the sensor receptacle 728 defined by the housing 720 is generally configured to removably retain the disposable sensor test strip 740 within the gas testing chamber 726. In various embodiments the sensor receptacle 728 is configured to slidably receive the disposable sensor test strip 740 that is manually inserted by a user. In some embodiments, the disposable sensor test strip 740 can be inserted with its long (or major) axis parallel to the long (or major) axis of the housing 720. However, in other embodiments, the disposable sensor test strip 740 can be inserted with its long (or major) axis positioned differently with respect to the long (or major) axis of the housing 720, such as perpendicular. Example sensor test strips will be described in more detail, below.

While FIG. 7 depicts the test strip located approximately in the middle of the gas sampling device 710 (top to bottom with regard to the perspective of the figure), it will be appreciated that the test strip can be positioned biased toward the top or the bottom, to be closer to an exterior surface of the housing 720 or gas sampling device 710. In some cases this can facilitate easier wireless reading of the disposable sensor strip by the docking station while the disposable sensor strip is still held within the housing. In some embodiments, the disposable sensor strip can be positioned less than 5 cm, 4 cm, 3 cm, 2 cm, 1 cm, 0.5 cm, 0.2 cm or less from exterior surface (or exterior wall) of the housing 720.

The docking station 730 is generally configured to collect data generated from testing the gas sample. The docking station 730 has a reading device 732 having communication hardware to wirelessly receive data through the housing of the gas sampling device 710. In many embodiments the reading device 732 of the docking station 730 is configured to wirelessly receive data from the disposable sensor test strip 740. In various embodiments, the reading device 732 can also be configured to wirelessly receive baseline data through the housing of the gas sampling device 710—from the disposable sensor test strip 740—where the term "baseline data" is defined as data collected before exposure of the disposable sensor test strip 740 to the gas sample or the patient or test subject. In some cases the baseline data can reflect conditions of whatever gas happens to be in the testing chamber prior to obtaining a gas sample of a patient. However, in other embodiments, ambient air can purposefully be pushed through the testing chamber, and/or a particular reference gas sample of known composition can be put into the testing chamber for purposes of generating baseline data. The communication hardware of the reading device 732 can be capable of near field communication with the disposable sensor test strip 740. In some embodiments the communication hardware of the reading device 732 is a near field electrode or near field reading circuit that is configured to receive patient data from a passive electrical circuit, such as by detecting a resonant frequency of an LRC resonator circuit and/or changes to the same.

In some embodiments the docking station has a proximity sensor that is configured to detect when the gas sampling device 710 is in sufficient proximity to the docking station 730 to collect data. And, although not currently depicted, in some embodiments the disposable sensor test strip 740 can have identifying information disposed thereon, other than the baseline or patient sample data, that can be read by a docking station or another device such as an identification code, radio frequency identification (RFID) tag, barcode, serial or id numbers, or other indicia. In such embodiments the docking station 730 (FIG. 7) can be configured to read, collect, save, and/or potentially transmit that identification data.

The docking station 730 is generally configured to be a docking location for the gas sampling device 710. The docking station 730 is generally configured to physically receive the gas sampling device 710. The docking station 730 can receive the gas sampling device 710 through a variety of structures and configurations that will be appreciated by those having ordinary skill in the art. In various embodiments the docking station 730 and the docking structure 721 of the gas sampling device 710 have a mating configuration by which the docking station 730 receives the docking structure 721 of the gas sampling device 710. In some such embodiments the docking station 730 and the docking structure 721 define an interference fit. However, in other embodiments, the docking station 730 can simply rest upon or in the docking structure 721. In some embodiments the docking station 730 and the docking structure 721 are configured to position the disposable sensor test strip 740 and the reading device 732 in sufficient proximity to accommodate transmission of data between the reading device 732 and disposable sensor test strip 740. In some embodiments the docking station and the docking structure are configured to position the disposable sensor test strip 740 and the reading device 732 within 6 cm, 5 cm, 4 cm, 3 cm, or 2 cm of each other, or even within 1 cm of each other.

The docking station 730 can have various additional components. In some embodiments the docking station 730 has a processor 736 and memory 735. The processor 736 and memory 735 can be configured to process and store data obtained from tested the gas sample. For example, the memory 735 can store baseline data locally and the processor 736 can be configured to remove collected baseline data from the tested gas data to obtain adjusted data. Such adjusted data can remove some impact of the ambient environment on the tested gas data. In another example, the processor can be configured to compare the adjusted data (or, in some embodiments the tested gas data) to known data indicative of one or more diseases. Such a comparison can be used to identify the presence of a particular disease using a comparative algorithm. In yet another example, the processor of the docking station 730 can be configured to identify a defect in the disposable sensor test strip 740. Example defects can include manufacturing defects and/or premature exposure to ambient gases. The docking station 730 can be configured to collect, save, and potentially transmit records of such defects.

The docking station 730 has networking hardware 734 in various embodiments. The networking hardware 734 can be configured to transmit data over a network to a remote system, including a cloud-based system. In some implementations the remote system can be a hospital, clinic, laboratory, or other location. In some embodiments the networking hardware 734 is configured to transmit data generated from testing the gas sample. The networking hardware 734 is configured to transmit baseline data in some embodiments. The networking hardware is configured to transmit adjusted data in some embodiments. In some embodiments the remote system analyzes the data it receives. For example, in some embodiments the remote system is configured to compare the adjusted data to known data indicative of a plurality of diseases. That comparison can identify the presence of a particular disease.

In some embodiments the docking station 730 has a user interface 738. The user interface 738 can be configured to communicate information to a user. For example, the user interface 738 can be configured to communicate an active data transmission, such as a data transmission between the docking station 730 and the gas sampling device 710 and/or between the docking station 730 and a network. In some embodiments the user interface 738 can be configured to communicate information about the current stage of the testing process, progress of the same, or what steps are next or what actions are required. For example, in some cases the user interface 738 can be configured to communicate that that the gas sampling device 710 is ready to receive a gas sample or that the docking station 730 has finished reading data from the gas sampling device 710. The user interface 738 can also be configured to communicate a defect in the sensor test strip. The user interface 738 can be configured to communicate through visual notification, audio notification, and the like. As a specific example, a flashing light can be used to indicate that the docking station 730 is transmitting data. The user interface 738 can include a light source such as an LED or similar light emitting device.

One example approach to using the system depicted in FIG. 7 will now be described. A disposable sensor test strip 740 is inserted into the gas sampling device 710 such that it is received by the gas testing chamber 726 defined by a housing of a gas sampling device. The gas sampling device 710 having the disposable sensor test strip 740 is docked to the docking station 730, and the reading device 732 of the docking station 730 reads baseline data from the disposable sensor test strip 740 through the housing 720 of the gas sampling device 710. The gas sampling device 710 is undocked from the docking station 730 after reading the baseline data, and a gas sample is received by the gas testing chamber such that the gas sample is brought into contact with the disposable sensor test strip 740. For example, the gas sampling device 710 may be physically grasped by a care provider and removed from the docking station 730 and physically handed to a patient or test subject who may then blow into the gas sampling device 710 to provide the gas sample to be analyzed. In other cases, the gas sampling device 710 may be held by the care provider instead of being held by the patient or test subject. The gas sampling device 710 can then be docked to the docking station 730 after receiving the gas sample, and the data from the tested gas is read from the disposable sensor test strip 740 by the reading device 732, wherein the adjusted data is read through the housing 720 of the gas sampling device 710. In various embodiments the disposable sensor test strip 740 is configured to be single-use. As such, the disposable sensor test strip 740 can be disposed of following the collection of sample gas data from the disposable sensor test strip 740. Various other methods of using the system depicted in FIG. 7 are also contemplated.

The measurement zones 742 can include a plurality of discrete binding detectors that can include one or more analyte binding receptors bound thereto. In some embodiments, all of the analyte binding receptors within a particular discrete binding detector can be the same with respect to their analyte binding properties. In other embodiments, at least some of the analyte binding receptors within a particular zone can be different from one another with respect to their analyte binding properties. In some embodiments, each discrete binding detector can be unique. In some embodiments, discrete binding detectors that are unique can be cross-reactive in that they bind to different portions or different configurations of the same chemical compound. In some embodiments, each discrete binding detector can include a single passive sensor circuit. In other embodiments, each discrete binding detector can include multiple passive sensor circuits.

In some embodiments, the passive sensor circuit can include a graphene varactor (variable capacitor) or metal-graphene-oxide capacitor (wherein RS represents the series resistance and CG represents the varactor capacitor) coupled to an inductor. Graphene varactors can be prepared in various ways and with various geometries. As just one example, in some aspects, a gate electrode can be recessed into an insulator layer. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a material, such as, aluminum oxide, hafnium dioxide, zirconium dioxide, hafnium silicate or zirconium silicate. A graphene layer can be disposed on the dielectric layer. In some aspects, the graphene layer can be a graphene monolayer. Contact electrodes can also be disposed on a surface of the graphene layer. Aspects of exemplary graphene varactors can be found in U.S. Publ. App. No. 2014/0145735, the content of which is herein incorporated by reference.

In various embodiments, the functionalized graphene layer (e.g., functionalized to include analyte binding receptors), which is part of the graphene varactor and thus part of a sensor circuit such as a passive sensor circuit, is exposed to the gas sample flowing over the surface of the measurement zone. The passive sensor circuit can also include an inductor. In some embodiments, only a single varactor is include with each passive sensor circuit. In other embodiments, multiple varactors are included, such as in parallel, with each passive sensor circuit.

In the passive sensor circuit, the quantum capacitance of the electrical circuit changes upon binding between the analyte binding receptors and a component from a gas sample. The passive sensor circuit can function as an LRC resonator circuit, wherein the resonant frequency of the LRC resonator circuit changes upon binding with a component from a gas sample.

The reading circuit can be used to detect the electrical properties of the sensor circuit. By way of example, the reading circuit can be used to detect the resonant frequency of the LRC resonator circuit and/or changes in the same. In some embodiments, the reading circuit can include a reading coil having a resistance and an inductance. When the sensor-side LRC circuit is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and the value of the phase dip frequency. Other techniques of reading graphene sensors can also be used.

Further aspects of gas and/or breath sampling systems are described in U.S. Publ. Appl. No. 2016/0109440, the content of which is herein incorporated by reference.

In some cases, the individual pieces of data gathered may be independent and distinct from one another. In other cases, some individual pieces of data can be associated with and/or correlated with other pieces of data and used for various purposes including, but not limited to, controls and/or validation data.

Figure 8:
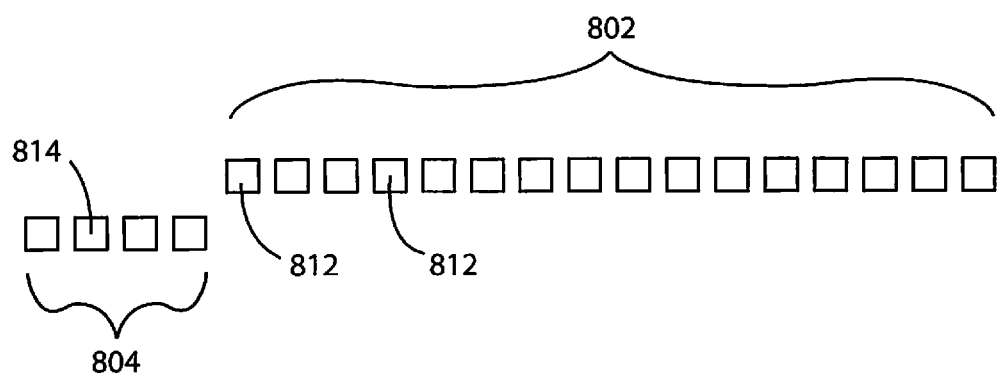
FIG. 8 is a diagram showing correspondence of various pieces of data collected from a gas sample along with various pieces of data indicative of sympathetic nervous activity.

Referring now to FIG. 8, a schematic representation is shown of various pieces of data that can be combined to form a combined data set for use in later operations such as machining learning analysis and/or pattern matching. In FIG. 8, the combined data can include volatile organic compound data 802, such as that which can be generated using gas or breath sampling devices as described herein. The volatile organic compound data 802 can include a plurality of individual pieces 812 of data. The combined data can also include data regarding the patient's sympathetic nervous activity 804. It will be appreciated that in some embodiments the combined data can include any of the types of data described herein. In some embodiments, the data regarding the patient's sympathetic nervous activity 804 can include a plurality of individual pieces of data 814. In this schematic view, all of the individual pieces of data (812 and 814) are independent and distinct.

Figure 9:
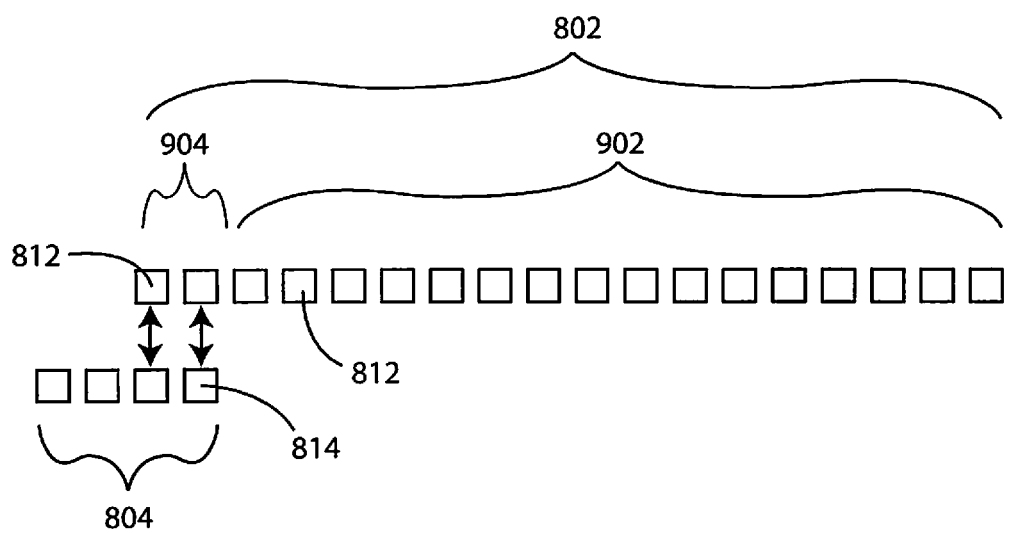
FIG. 9 is a diagram showing correspondence of various pieces of data collected from a gas sample along with various pieces of data indicative of sympathetic nervous activity.

Referring now to FIG. 9, another schematic representation is shown of various pieces of data that can be combined to form a combined data set for use in later operations such as machining learning analysis and/or pattern matching. In FIG. 9, the combined data can include volatile organic compound data 802, such as that which can be generated using gas or breath sampling devices as described herein. The volatile organic compound data 802 can include individual pieces of data 812 broken up into a first set of data 902 that is independent and distinct from other pieces of data and a second set of data 904 that is related to or correlates to certain other pieces of data, such as data regarding the patient's sympathetic nervous activity 804, or other types of data. In this manner, the first set of data 902 can be used in various ways such as a control or otherwise for validation purposes before the data is combined.

Sensors and Data

In various embodiments herein, the patient-specific device and/or other devices or systems that may be part of a system can collect data regarding a patient's autonomic tone, or in some embodiments more specifically, a patient's sympathetic nervous system activity. However, it will be appreciated that measurement of autonomic tone (e.g., parasympathetic/sympathetic balance) or measurement of parasympathetic tone can also be performed in addition to or instead of measurement of sympathetic nervous activity in some embodiments. In some embodiments other types of data can also be included such as demographic data, medical record data, measurements of environmental conditions, patient activity data, indications of symptoms, information regarding the current or past physical state of the patient, and the like.

Many different measures of sympathetic nervous activity can be gathered and/or evaluated. In some embodiments, measures of sympathetic nervous activity herein can include one or more of heart rate variability (HRV), electrodermal activity (EDA), blood pressure, respiratory rate, respiratory sinus arrhythmia (RSA), and baroreceptor sensitivity (BRS).

Many different specific sensors can be used to gather data that reflects sympathetic nervous activity. In some embodiments, an ECG sensor can be used. The ECG sensor can include at least two electrodes disposed in the patient's body configured to detect electrical activity from the patient's body. A processor circuit can use the electrogram information to identify morphological characteristics (e.g., timings, amplitudes, shapes, etc.).

Specific features from an ECG sensor can include, but are not limited to, RR interval/heart rate; P-wave detection (or a surrogate); Q-wave detection (or a surrogate); intervals between any of the features of a PQRST waveform; heart rate variability (HRV); heart rate density index of heart rate; AVNN (average of all NN intervals); SDNN (standard deviation of all NN intervals)—which is a measure of long term heart rate variability (HRV); SDANN (standard deviation of the averages of NN intervals in all 5-minute segments of a 24-hour recording)—which is a measure of long term HRV; SDNNIDX (mean of the standard deviations of NN intervals in all 5-minute segments of a 24-hour recording); RMSSD (square root of the mean of the squares of differences between adjacent NN intervals)—which is a measure of short term HRV); pNN50 (percentage of differences between adjacent NN intervals that are greater than 50 ms); power spectrum of HRV signal to determine overall spectral density in Very Low frequency (VLF) band, Low Frequency (LF) band, and High Frequency (HF) band; ratios of either two of VLF, LF, and HF bands; QRS complex amplitude or morphology, or surrogate thereof; match between ECG waveform and optimal morphology template (the optimal template can be defined and/or updated by a physician or internal algorithm based on morphology during times of good therapy), the match can be quantified using correlation between the two signals or can be quantified by when a given signal leaves an interval around the mean defined by, for example, twice the standard deviation; PP interval; PR interval; QRS azimuth; QRS duration; ST segment; QRS-T angle; QT interval; or dimensions obtained through dimensionality reduction of the entire waveform such as principal components analysis.

In some embodiments, a blood volume pulse (BVP) sensor can be used. In some embodiments, the BVP sensor can be a photoplethysmography (PPG) sensor, and the pulsatile information (including timing, shape, and morphology) can obtained by passing light through the neighboring artery. Aspects of PPG sensors are described in U.S. Pat. No. 8,494,606 and U.S. Publ. Appl. No. 2017/0042435, the content of which is herein incorporated by reference. In some embodiments, the BVP sensor can measure externally from a finger, wrist, ear, etc. In some embodiments, the BVP sensor can measure internally near an artery. In some embodiments, the BVP sensor is an electrical bioimpedance/impedance cardiography sensor, and the pulsatile information (including timing, shape, and morphology) is obtained by measuring change in impedance across artery as blood flow changes. In some embodiments, the BVP sensor is an accelerometer, and pulsatile information (including timing, shape, and morphology) is obtained by measuring changes in position as shape of artery changes during blood flow. In some embodiments, the BVP sensor is a pressure sensor around or nearby the artery, and the pulsatile information (including timing, shape, and morphology) is directly measured from artery. In some embodiments, the BVP sensor is a pressure sensor inside the artery, and the pulsatile information (including timing, shape, and morphology) is directly measured within the artery.

Specific features from a BVP sensor can include match between a BVP waveform and an optimal morphology template (the optimal template can be defined and/or updated by a physician or internal algorithm based on morphology during times of good therapy and a match can be quantified using correlation between the two signals or by when a given signal leaves an interval around the mean defined by, for instance, twice the standard deviation); systolic amplitude; diastolic amplitude; area under BVP waveform; pulse rate variability (calculated in any measure similar to HRV from ECG); pulse transit time; DC component of BVP waveform; AC component of BVP waveform; dicrotic notch amplitude; time between systolic and diastolic peaks; or dimensions obtained through dimensionality reduction of the entire waveform such as principal components analysis.

In some embodiments, an electrodermal activity (EDA) sensor can be used. Aspects of electrodermal sensors are described in U.S. Publ. Appl. No. 2017/0014043, the content of which is herein incorporated by reference. The surface electrode can measure skin conductance from, the hand (palmar surface), the foot (plantar surface), the wrist (such as incorporated into a wrist worn monitoring device), or an implanted device that is communicatively coupled to a conductive layer (tattoo) anywhere on the skin.

In some embodiments, a blood pressure sensor can be used. In various embodiments, blood pressure can be derived from heart sounds signal, a BVP signal, a blood pressure cuff, or the like.

In some embodiments, a respiration sensor can be used. In various embodiments, respiration can be sensed through contact based methods, through chest and abdominal movement detection, through acoustic based measures, airflow monitoring, a muscle strain sensor, or impedance based measures. Non-contact methods can also be used to detect respiration.

The respiration sensor can be an implantable sensor configured to monitor subject chest expansion and contraction. In an example, the respiration sensor can be configured to provide information about a subject's tidal volume or minute ventilation. In some embodiments, the respiration sensor can be an acoustic sensor. The acoustic sensor can be an implantable transducer such as a microphone or accelerometer. The acoustic sensor can be configured to receive acoustic vibrational energy from a subject, such as in the audible spectrum. In an example, a portion of the circuitry can be configured to receive information from the acoustic sensor and identify respiration information. In some embodiments, the respiration sensor can be a vibration sensor. The vibration sensor can be an implantable transducer, such as an accelerometer. The vibration sensor can be configured to receive vibrational energy from a patient and can be used to identify respiration information. In some embodiments, the respiration sensor can be an impedance sensor configured to determine respiration data. The impedance sensor can include at least two electrodes disposed in the patient's body and configured to detect electrical signals therein. The device can be configured to receive electrical signal information from the impedance sensor to identify a detected or measured impedance between the two or more electrodes. In an example, a processor circuit can be used to process the received impedance information to identify respiration data.

Specific features from a respiration sensor can include absolute HRV during inspiration and expiration; ratio of HRV during inspiration to expiration; absolute HR during inspiration and expiration; and change in HR over respiration cycle.

Pulmonary data can be used in some embodiments. Pulmonary data can include forced expiratory volume in 1 second (FEV1), forced vital capacity (FVC), FEV1/FVC, or various other lung function/spirometry test parameters. In some embodiments capnography can be used to gather data herein. In various embodiments, data indicative of a change in the pulomonary condition can be used including lung sounds, trans-thoracic impedance, vocal expression, and the like.

In some embodiments, an EEG sensor can be used. The EEG sensor can be embodied as electrodes in an EEG cap, EEG headsets, ear EEG devices, implanted subdermal wireless electrode(s) implant, implanted neuromodulation leads (e.g. occipital, trigeminal, deep brain stimulation leads), or other EEG measuring devices within sunglasses, hats, patches, etc.

In some embodiments, data from a sensor such as an electrogastrogram (EGG) can also be used. Aspects of electrogastrograms are described in U.S. Pat. No. 5,704,368, the content of which is herein incorporated by reference.

In some embodiments, an NIRS (near-infrared spectroscopy) sensor can be used. The NIRS sensor can be embodied as an individual NIRS optode, a multi-optode NIRS (e.g. measured using a cap, similar to EEG), a subdermal optode(s) implant. Aspects of NIRS sensors are described in U.S. Publ. Appl. No. 2014/0051956, the content of which is herein incorporated by reference.

EEG/NIRS features can include dominant frequency, spectral power (relative and absolute), including total power as well as individual spectral power for specific brain wave frequencies (alpha, beta, theta, etc.); coherence, cross-coherence, spectral entropy, mutual information, and other correlation measures; changes (frequency shifting) in the dominant amplitude peak for relevant frequency bands, q-factor based metrics; and other EEG/NIRS-specific metrics.

In some embodiments, the sensor can be an activity or gait sensor. For example, the sensor can one or more of a 3-axis accelerometer, 3-axis gyroscope, and/or 3-axis magnetometer. In some embodiments, the sensor can be an electromyography (EMG) sensor.

Baroreceptor reflex sensitivity (BRS) features can be calculated using measures such as blood pressure; heart rate or inter-beat Interval (IBI); heart rate variability; change in heart rate—captured as a slope of change or as a time interval for the parameter to reach X % of the peak change; change in blood pressure—captured as a slope of change or as a time interval for the parameter to reach X % of the peak change. BRS can be classified based on the level of physical activity or exertion indicated by the activity and respiration sensors (e.g., mild activity, moderate activity, or vigorous activity). BRS can characterized over a continuum of levels of physical activity or exertion indicated by the activity and respiration signals, for example, by vector magnitude units (in g) over a period of time, caloric expenditure, distance traveled, or other activity or exertion measures, or a combination thereof.

Aspects from medical records can also be used as data herein. Examples of such data include, but are not limited to, medication information, previous symptoms, previous diagnoses, previously obtained diagnostic test results, previous medical procedures performed on the patient, and the like.

Data herein can include sleep data. Sleep data can include, but is not limited to, average sleep duration, REM sleep cycles and durations, sleep quality, activity during sleep, sleep apnea incidents, breathing patterns during sleep, waking episodes, morning waking time, and the like.

In addition to other types of data described herein, in some embodiments demographic features from patient can be used, including but not limited to, age, sex, geography, and/or ethnicity. Other types of data can include the time of day when measurements are taken.

In some embodiments, external environmental condition data can also be used. Environmental condition data can include, but is not limited to, humidity, external temperature, current weather, pollution level and the like.

In some embodiments, data regarding the patient's use of, or irregular patterns regarding, the Internet, social media, Internet searches, and the like can be used.

Methods

Embodiments herein can include various methods. Exemplary methods can include any of the approaches and/or operations described herein. In an embodiment, a method of assessing the health status of a patient is included. The method can include evaluating the presence of volatile organic compounds in a breath or gas sample of the patient to generate volatile organic compound data. The volatile organic compound data can be gathered using systems and devices such as those described herein.

In some cases, the volatile organic compound data can reflect the output of a plurality of graphene sensors. The plurality of graphene sensors can include sensors that are specific for different volatile organic compounds. In some embodiments, the plurality of graphene sensors can detect the presence of at least 5, 10, 15, 20, 30, 40 or more different volatile organic compounds. In some embodiments, the number of different volatile organic compounds detected by the graphene sensors can be in a range wherein any of the forgoing numbers can serve as the upper or lower bound of the range provided that the upper bound is greater than the lower bound.

In some embodiments, one or more of the plurality of graphene sensors are chosen as controls on the collected data regarding the patient's sympathetic nervous activity. In some embodiments, the controls correlate with sympathetic nervous activity. In some embodiments, the method can include generating a notification if the measured values of the controls do not match what would be expected for the measured values of sympathetic nervous activity.

The method can further include collecting data regarding the patient's sympathetic nervous activity. In specific, the data regarding the patient's sympathetic nervous activity can include changes in the patient's sympathetic nervous activity and/or trends regarding the same. Sympathetic nervous activity can be gathered in either a clinical or a non-clinical environment. In some embodiments, data regarding the patient's sympathetic nervous activity can be gathered using a wearable device and/or an implanted device. In some embodiments, the collected data regarding the patient's sympathetic nervous activity reflects a baseline level of sympathetic nervous activity and changes over the baseline level of sympathetic nervous activity.

Many different types of data that reflect a patient's sympathetic nervous activity can be used. However, in some embodiments, the data regarding the patient's sympathetic nervous activity can be selected from the group consisting of heart rate variability (HRV), electrodermal activity (EDA), blood pressure, respiratory rate, respiratory sinus arrhythmia (RSA), and baroreceptor sensitivity (BRS).

In some embodiments, data regarding the patient's sympathetic nervous activity can be gathered over a period of time. In some embodiments, collecting data regarding the patient's sympathetic nervous activity is performed over a time period of at least about 1 second, 5 seconds, 10 seconds, 15 seconds, 30 seconds, 60 seconds, 5 minutes, 10 minutes, 20 minutes, 30 minutes, 45 minutes, 60 minutes, 2 hours, 4 hours, 8 hours, 12 hours, 24 hours, 2 days, 3 days, 4 days, 5 days, 10 days, 15 days, 20 days, 30 days, 45 days, 60 days, 90 days, 120 days or more. In some embodiments, the data can be collected over a time period in a range wherein any of the foregoing times can serve as the upper or lower bound of the range, provided that the upper bound in greater than the lower bound. While not intending to be bound by theory, it is believed that the longer the duration, the more data will exist on the patient's baseline state and the better the ability to detect or predict any excursion from the baseline state.

Regardless of where the data is gathered, in many embodiments, the data can be exchanged with other devices and/or other components of a system. In some embodiments, the volatile organic compound data from a breath sample of the patient is downloaded onto at least one of a wearable device and an implantable device from an external breath testing device. In some embodiments, collected data regarding the patient's sympathetic nervous activity is uploaded from a wearable device to clinical diagnostic device.

The method can further include combining the volatile organic compound data with the collected data regarding the patient's sympathetic nervous activity to form a combined data set. In some cases, all pieces of data in the combined data set can be weighted equally. In other cases, some of the pieces of data in the combined data set can be weighted more heavily than others. In some embodiments, some pieces of data may simply serve as a control.

It will be appreciated that although the combined data set frequently includes volatile organic compound data and data regarding the patient's sympathetic nervous state, still other types of data can be added into the combined data set, such as other types of data described herein. For example, in some embodiments the method can also include collecting data regarding the patient's functional status. The data regarding the patient's functional status can be selected from the group consisting of gait and accelerometry data. In some embodiments, the method can also include adding the data regarding the patient's functional status to the combined data set.

The method can further include comparing the combined data set against one or more previously determined patterns using a pattern matching or pattern recognition algorithm to determine the pattern that is the best match, wherein the specific previously determined pattern that is the best match indicates the health status of the patient.

By way of example, patterns amongst large sets of patient data may be originally identified through machine learning analysis or another similar algorithmic technique. For example, a training set of data including: 1.) information regarding volatile organic compounds for a set of patients, 2.) information regarding sympathetic nervous state or activity for the same set of patents, 3.) information regarding specific diagnoses or other health statuses for the same set of patients, and/or 4.) other types of data described herein can be processed with a machine learning algorithm or similar algorithmic technique in order to generate one or more patterns of volatile organic compounds, sympathetic nervous state, and/or other data that correlate with certain diagnosis or health statuses.

Algorithms can be used to create new models using any of numerous machine learning techniques, or apply the results of previously calculated models using these techniques, such as logistic regression; random forest, or an artificial neural network.

Many different pattern matching or pattern recognition algorithms can be used. By way of example, in some embodiments a least squares algorithm can be used to identify a particular pre-determined pattern that a combined data set most closely matches.

In some embodiments, the patient can be prompted to take a breath or gas test (where the test could be performed either in a non-clinical setting such as their home or where such a prompt could cause them to come to a clinical setting to take the test).

In some embodiments, a pattern including such things as sleep patterns (e.g. wearable, implant or non-contact in-home sensor), physiological data (autonomic tone measures), body weight (such as weight automatically measured by a mat in the house), activity levels (e.g. mobile device, wearable, implant or non-contact in-home sensor), etc. can be assessed, such as using an algorithm, and if the results of those factors so indicate, then the system can inform the user that they should administer or get a breath or gas test to detect early signs of heart failure decompensation. If a positive result, or data trends are beyond a normal range for the individual patient, then the system can inform the patient to seek medical care for early intervention.

In some embodiments, a pattern including things such as sleep patterns, autonomic tone, respiratory rate, respiratory sounds, activity levels, etc., can be used to recommend to the user that they should administer a breath test (or come to a clinic to get a breath test) to detect early signs of a COPD exacerbation or repeat exacerbation. If a positive result, or data trends beyond normal range for the individual patient, seek medical care and/or use prescribed pharmaceutical (e.g. bronchodilators, corticosteroids, etc.) for early intervention.

Beyond, heart failure decompensation and COPD, such patterns and prompts to the patient to get a breath test can also be used for diabetes management and inflammatory bowel diseases (also including data regarding dietary intake, autonomic tone, etc. in the pattern) to detect early signs of a flare-up.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like. "Circuitry" can include both hardwired circuitry for execution of particular operations as well as processors that are programmed to execute instructions to provide the same functionality.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the scope to the precise forms disclosed herein. Rather, the embodiments are chosen and described so that others skilled in the art can appreciate and understand the principles and practices.

The invention claimed is:

1. A method of assessing the health status of a patient comprising:
    evaluating the presence of volatile organic compounds in a breath or gas sample of the patient with a plurality of graphene sensors to generate volatile organic compound data, wherein the plurality of graphene sensors include sensors that are specific for different volatile organic compounds;
    collecting data regarding the patient's sympathetic nervous activity, the data comprising at least one of heart rate variability (HRV), electrodermal activity (EDA), respiratory sinus arrhythmia (RSA), and baroreceptor sensitivity (BRS);
    combining the volatile organic compound data with the collected data regarding the patient's sympathetic nervous activity to form a combined data set; and
    matching the combined data set against one or more previously determined data patterns using a pattern matching algorithm to determine the data pattern that is the best match, wherein the specific previously determined data pattern that is the best match indicates the health status of the patient.

2. The method of claim 1, wherein the one or more previously determined data patterns are created using a machine learning process.

3. The method of claim 1, further comprising collecting data regarding the patient's functional status, the data comprising gait data; and
    adding the data regarding the patient's functional status to the combined data set.

4. The method of claim 1, further comprising
    collecting data regarding the patient's demographic features; and
    adding the data regarding the patient's demographic features to the combined data set.

5. The method of claim 1, wherein collecting the data regarding the patient's sympathetic nervous activity is performed in a non-clinical setting and evaluating the presence of the volatile organic compounds is performed in a clinical setting.

6. The method of claim 1, wherein collecting the data regarding the patient's sympathetic nervous activity is performed with a wearable device.

7. The method of claim 1, wherein collecting the data regarding the patient's sympathetic nervous activity is performed over a time period of at least about 1 day.

8. The method of claim 1, wherein collecting the data regarding the patient's sympathetic nervous activity is performed with an implanted device.

9. The method of claim 1, wherein the volatile organic compound data from the breath or gas sample of the patient is downloaded from an external breath sensing system onto at least one of a wearable device and an implantable device.

10. The method of claim 1, wherein the collected data regarding the patient's sympathetic nervous activity is uploaded from a wearable device to a clinical diagnostic device.

11. The method of claim 1, wherein one or more of the plurality of graphene sensors are chosen as controls on the collected data regarding the patient's sympathetic nervous activity.

12. The method of claim 11, wherein the controls correlate with sympathetic nervous activity.

13. The method of claim 12, further comprising generating a notification if the measured values of the controls do not match the measured values of sympathetic nervous activity.

14. The method of claim 1, wherein the collected data regarding the patient's sympathetic nervous activity reflects a baseline level of sympathetic nervous activity and changes over the baseline level of sympathetic nervous activity.

15. The method of claim 1, wherein the plurality of graphene sensors can detect the presence of at least 10 different volatile organic compounds.

16. A diagnostic health system comprising:
    a communications circuit;
    a memory circuit; and
    a processor in electronic communication with the communication circuit and the memory circuit, the processor is configured to
        combine volatile organic compound data with collected data regarding a patient's sympathetic nervous activity to form a combined data set, the collected data comprising at least one of heart rate variability (HRV), electrodermal activity (EDA), respiratory sinus arrhythmia (RSA), and baroreceptor sensitivity (BRS); and
        match the combined data set against one or more previously determined data patterns using a pattern matching algorithm to determine a pattern that is the best match, wherein the specific previously determined pattern that is the best match indicates the health status of the patient; and
        report the health status of the patient based on the best pattern match.

17. The diagnostic health system of claim 16, wherein the diagnostic health system is a wearable device and the volatile organic compound data is downloaded onto the wearable device from another device.

18. The diagnostic health system of claim 16, wherein the diagnostic health system is disposed in a clinical environment and collected data regarding a patient's sympathetic nervous activity is uploaded to the diagnostic health system from a wearable device.

19. A diagnostic health system comprising:
a patient-specific device selected from the group consisting of a wearable device and an implanted device; and
an external breath sensing system; and
a processor receiving data from the patient-specific device and the external breath sensing system;
wherein the patient-specific device collects data regarding a patient's sympathetic nervous activity, the data comprising at least one of heart rate variability (HRV), electrodermal activity (EDA), respiratory sinus arrhythmia (RSA), and baroreceptor sensitivity (BRS);
wherein the external breath sensing system collects data regarding the presence of volatile organic compounds in a breath or gas sample of the patient; and
wherein the processor is configured to
combine the volatile organic compound data with the patient's sympathetic nervous activity data to form a combined data set; and
match the combined data set against one or more previously determined data patterns using a pattern matching algorithm to determine a pattern that is the best match, wherein the specific previously determined pattern that is the best match indicates the health status of the patient; and
report the health status of the patient based on the best pattern match.

\* \* \* \* \*